United States Patent [19]
Boden et al.

[11] Patent Number: 5,711,952
[45] Date of Patent: Jan. 27, 1998

[54] USE OF 7-ISOPROPYL--8, 8-DIMETHYL-6, 10-DIOXASPIRO-C₁₀ AND C₁₁ ALKANE DERIVATIVES FOR THEIR ORGANOLEPTIC PROPERTIES AND SYNTHESIS PROCESS FOR PREPARING SUCH DERIVATIES

[75] Inventors: Richard M. Boden, Ocean; Irene Burtyk, Clifton, both of N.J.; Jan Van Elst, Bilthoven, Netherlands; Marie R. Hanna, Hazlet; Charles E.J. Beck, Summit, both of N.J.

[73] Assignee: International Flavors & Fragrances Inc., New York, N.Y.

[21] Appl. No.: 812,040
[22] Filed: Mar. 6, 1997
[51] Int. Cl.⁶ .................................. A61K 6/00
[52] U.S. Cl. .................................. 424/401
[58] Field of Search .............. 549/333; 424/65, 424/401; 252/522

[56] References Cited

U.S. PATENT DOCUMENTS 4,606,849  8/1986  Ansari et al. .................. 252/522 R
5,451,404  9/1995  Furman ........................... 424/401

FOREIGN PATENT DOCUMENTS 2533048  2/1977  Germany ................. A61K 7/40
9630469  3/1995  WIPO.

*Primary Examiner*—Terressa Mosley
*Attorney, Agent, or Firm*—Arthur L. Liberman

[57] ABSTRACT

Described is the use of 7-isopropyl-8,8-dimethyl-6,10-dioxaspiro-$C_{10}$ and $C_{11}$ alkane derivatives defined according to the structure:

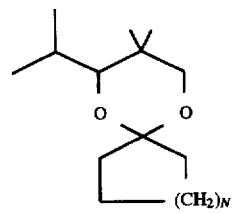

wherein N is 1 or 2 for their organoleptic properties, particularly for use in imparting, augmenting or enhancing the aroma of a perfume composition, perfumed polymer, detergent, fabric softener, or bleach composition. Also described is a process for preparing such 7-isopropyl-8,8-dimethyl-6,10-dioxaspiro-$C_{10}$ and $C_{11}$ alkane derivatives using as starting materials cycloalkanones defined according to the structure:

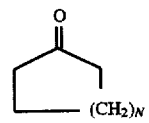

and the diol having the structure:

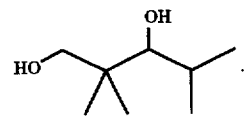

27 Claims, 15 Drawing Sheets

GLC PROFILE FOR EXAMPLE I.

GLC PROFILE FOR EXAMPLE I, FRACTION 5.

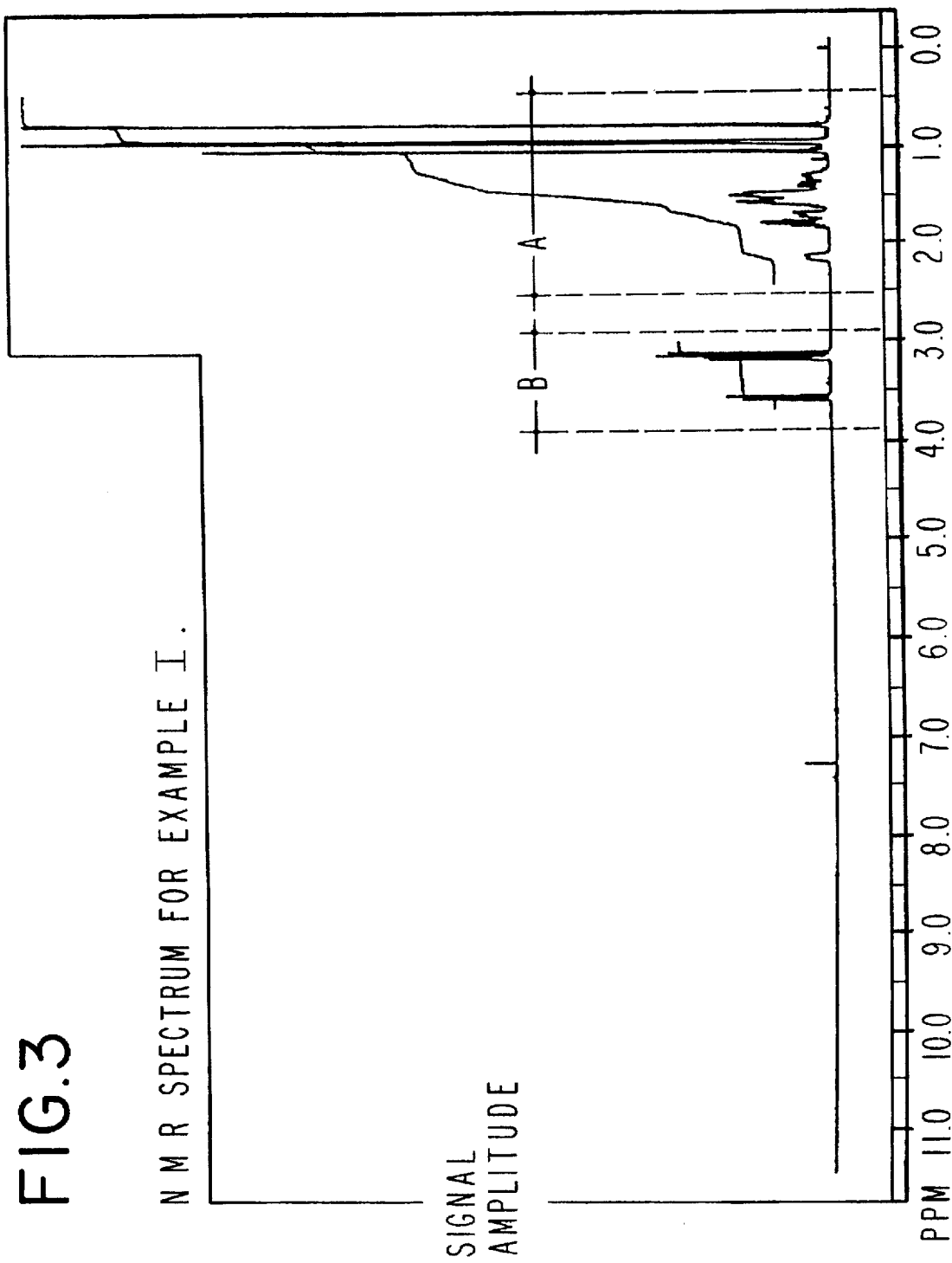
FIG. 3 NMR SPECTRUM FOR EXAMPLE I.

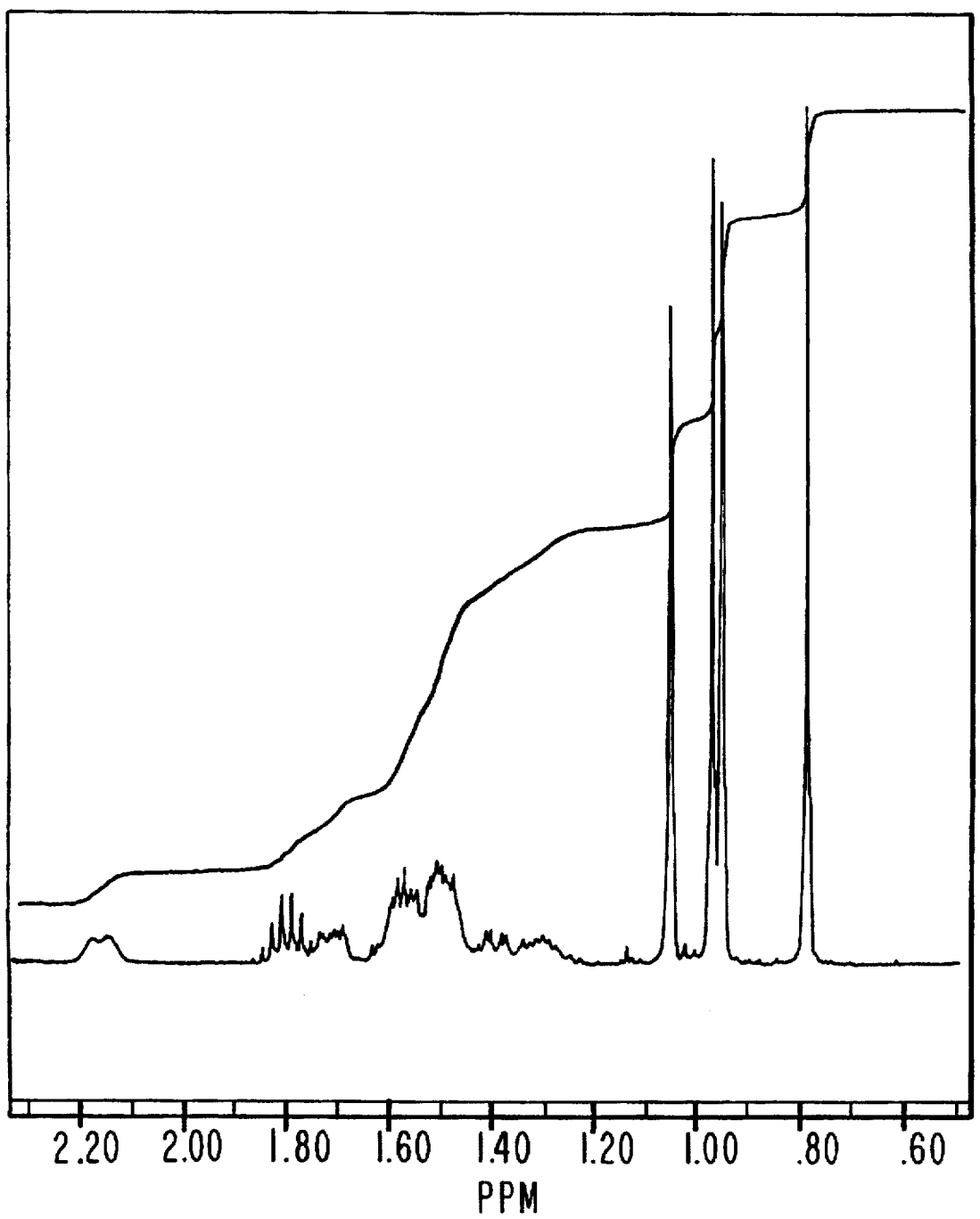
FIG. 3-A

FIG.3-B
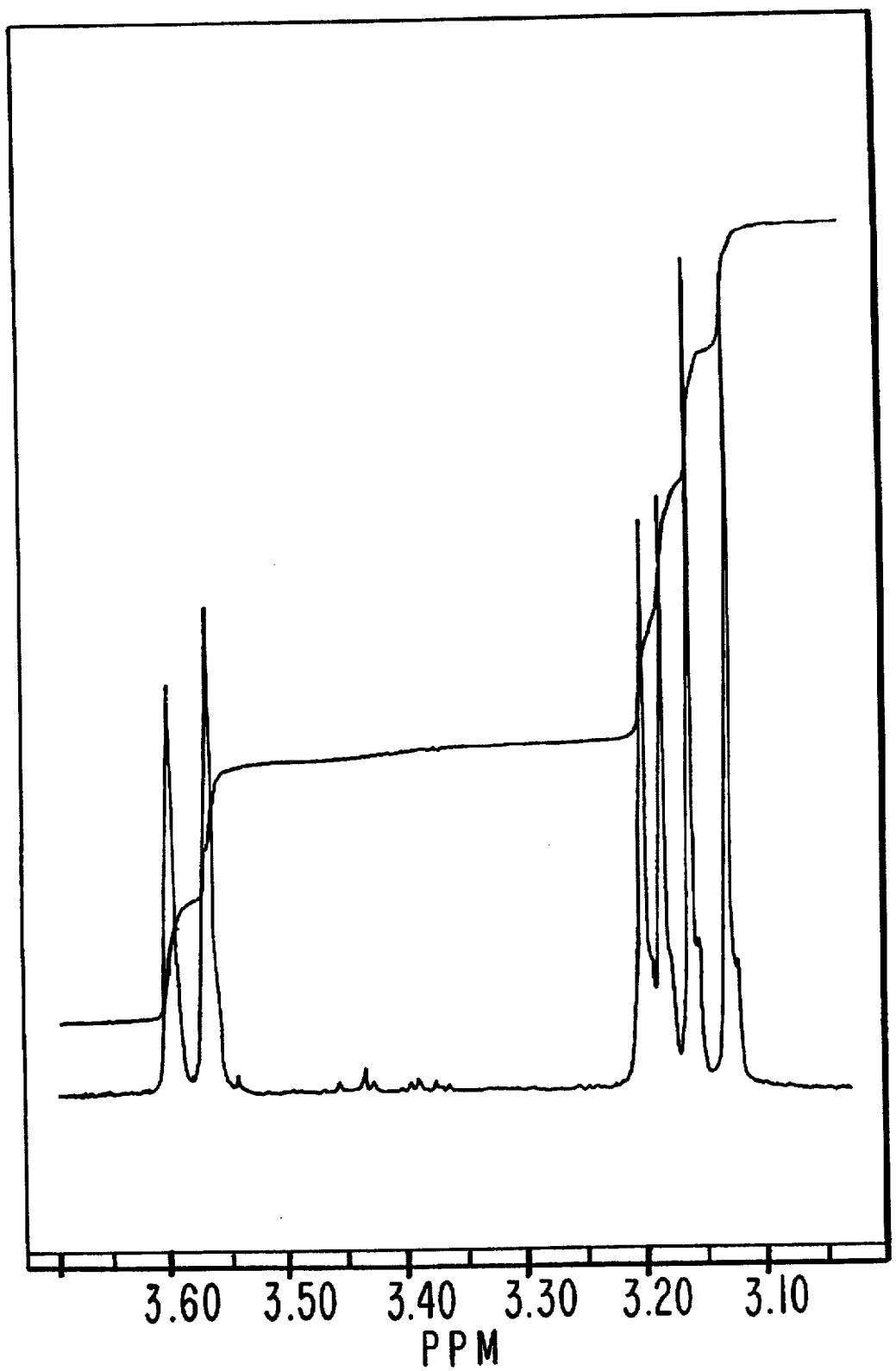

GLC PROFILE FOR EXAMPLE II (A).

GLC PROFILE FOR EXAMPLE II (A).

GLC PROFILE FOR EXAMPLE II (B).

GLC PROFILE FOR EXAMPLE III.

GLC PROFILE FOR EXAMPLE III, FRACTION 5.

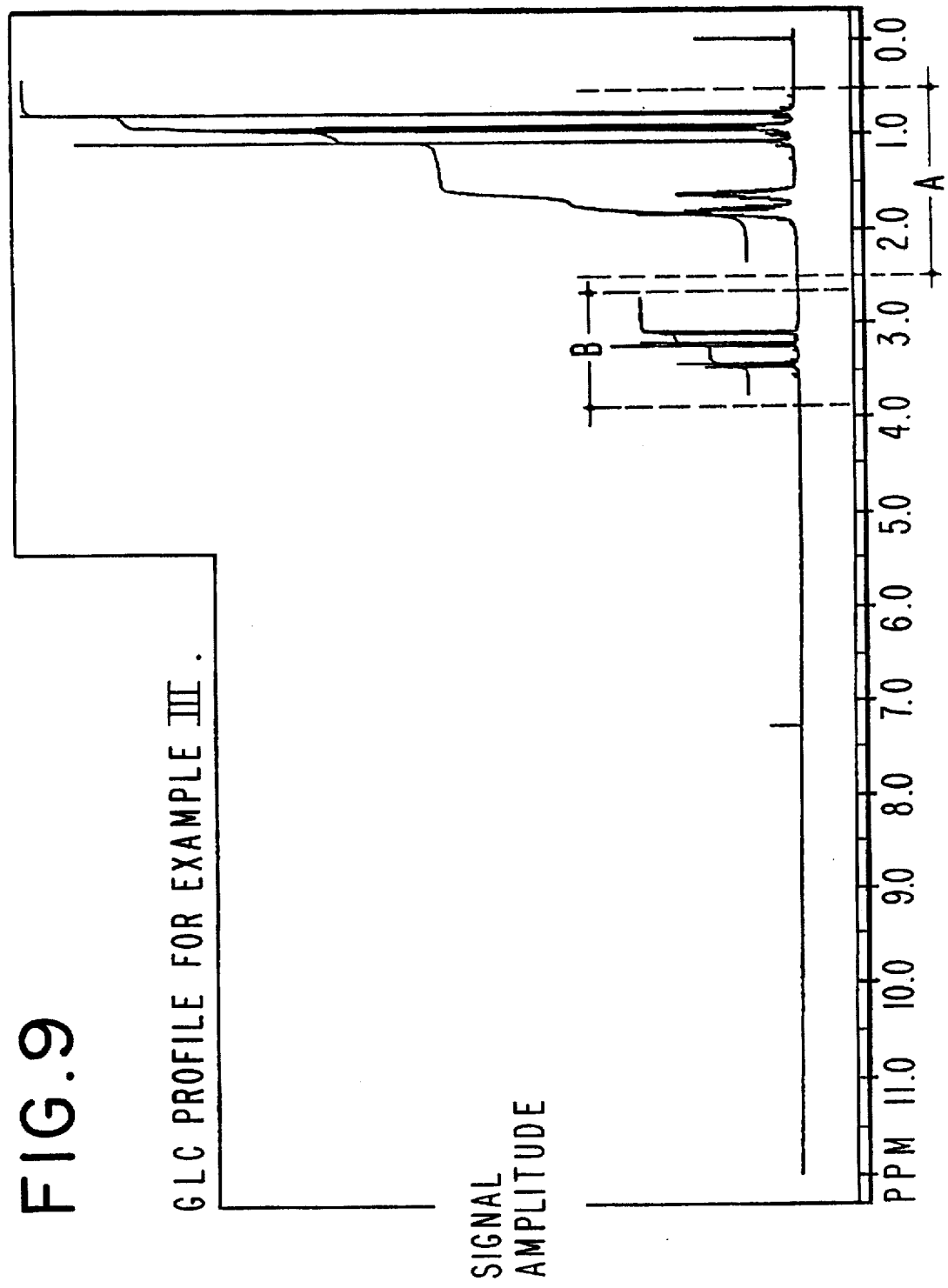

FIG.9-A
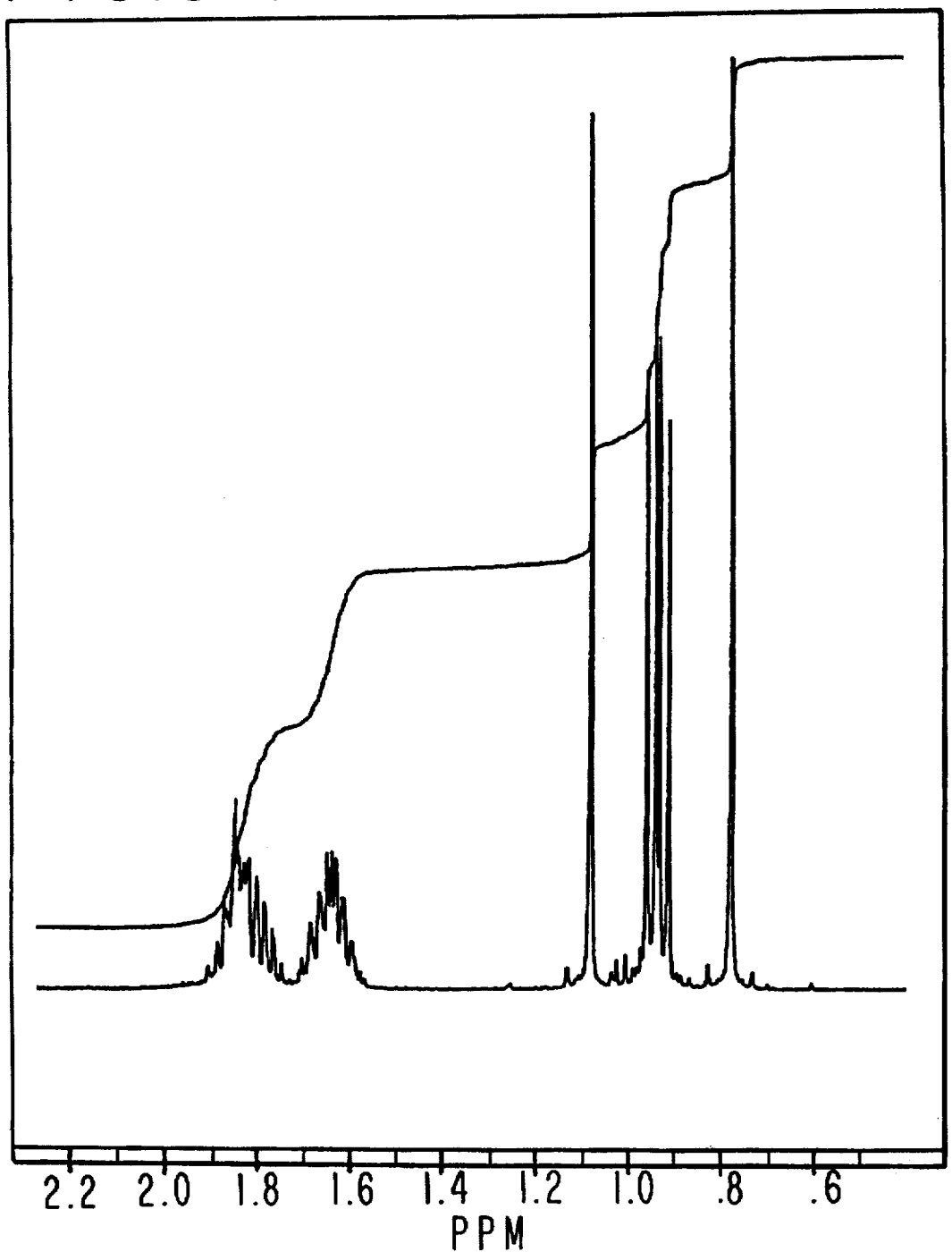

FIG. 9-B
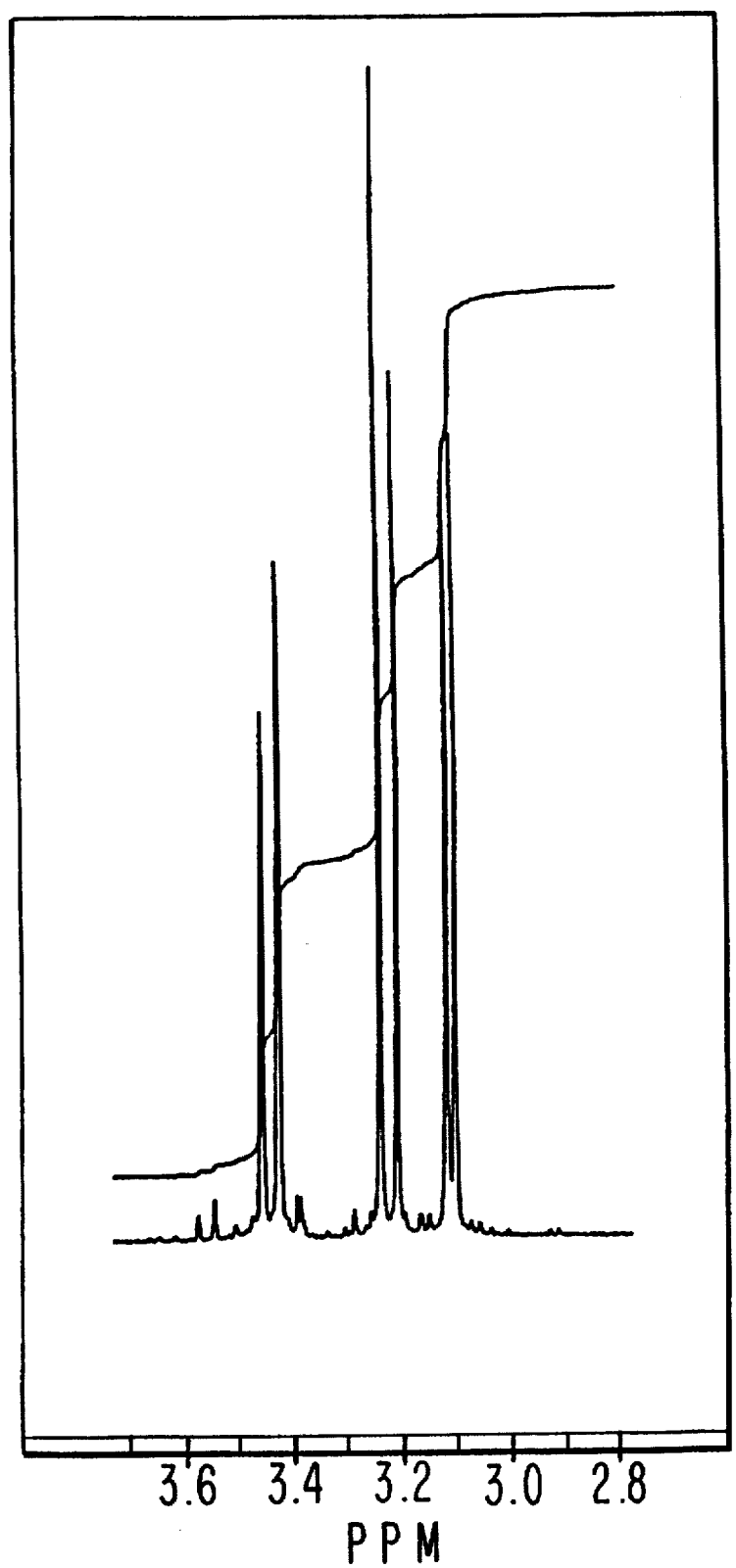

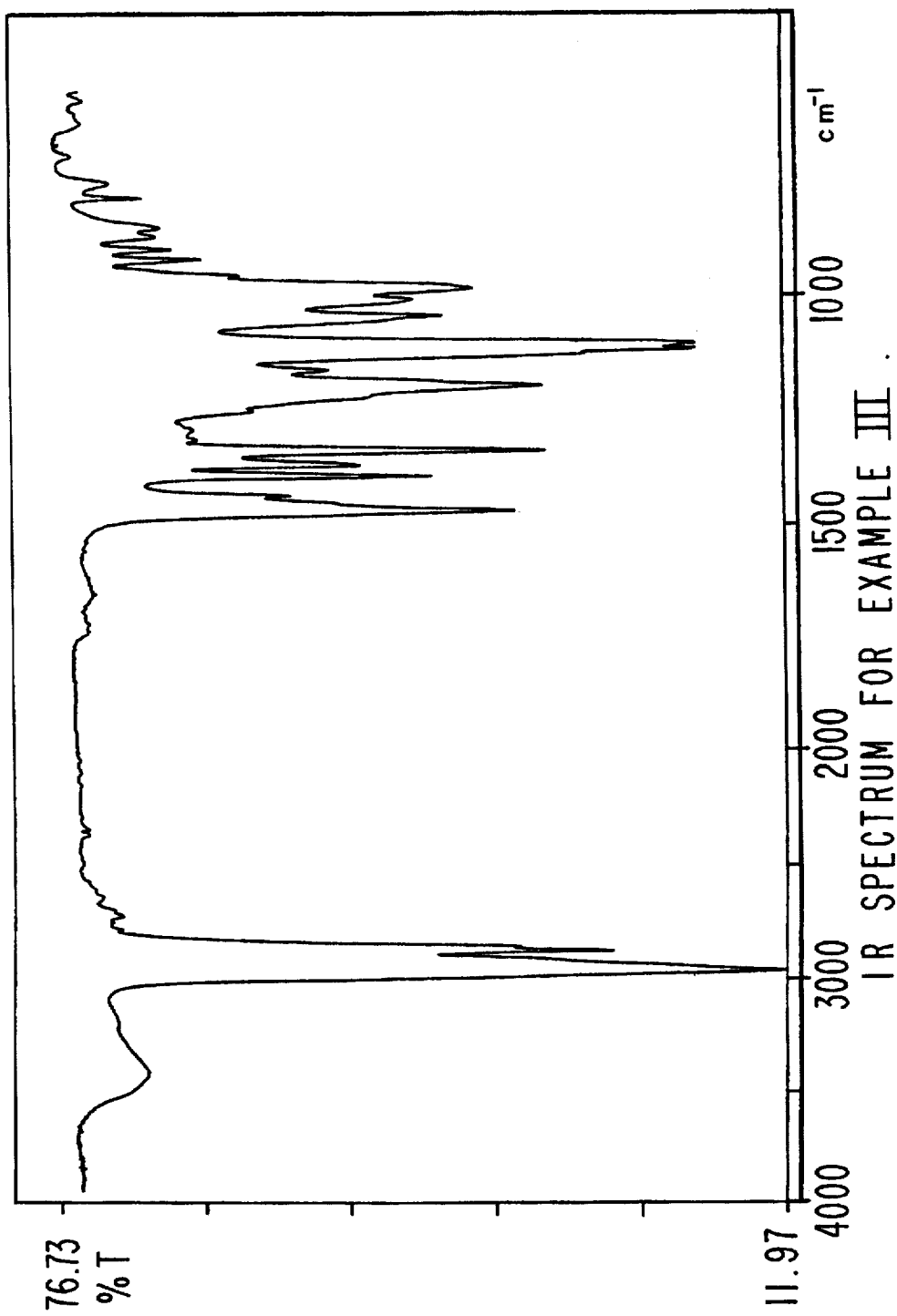
FIG.10 IR SPECTRUM FOR EXAMPLE III.

USE OF 7-ISOPROPYL- -8, 8-DIMETHYL-6, 10-DIOXASPIRO-C₁₀ AND C₁₁ ALKANE DERIVATIVES FOR THEIR ORGANOLEPTIC PROPERTIES AND SYNTHESIS PROCESS FOR PREPARING SUCH DERIVATIES

BACKGROUND OF THE INVENTION

Our invention is related to a process for imparting, augmenting or enhancing the aroma of a perfume composition, perfume polymer, soap, detergent, fabric softener or bleach composition by adding to such material an aroma imparting, augmenting or enhancing quantity and concentration of at least one 7-isopropyl-8,8-dimethyl-6,10-dioxaspiro-$C_{10}$ and $C_{11}$ alkane derivative defined according to the structure:

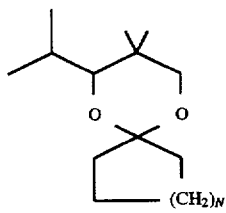

wherein N is 1 or 2. Our invention is also related to perfume compositions consisting essentially of a non-salicylate-containing perfume base and intimately admixed therewith an aroma augmenting or enhancing quantity and concentration of at least one 7-isopropyl-8,8-dimethyl-6,10-dioxaspiro-$C_{10}$ and $C_{11}$ alkane derivative defined according to the structure:

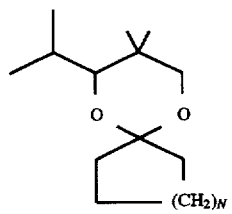

wherein N is 1 or 2. Our invention is further related to the process for preparing such 7-isopropyl-8,8-dimethyl-6,10-dioxaspiro-$C_{10}$ and $C_{11}$ alkane derivatives using as starting materials a cycloalkanone defined according to the structure:

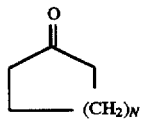

and a diol having the structure:

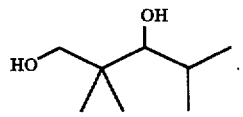

Inexpensive chemical compounds which are substantive and long-lasting and which can provide strong, persistent minty, sage, guaiac wood, pepper, fruity, herbal, woody, sweet, balsamic, chamomile, jasmine, eucalyptus and anisic aromas with minty, sage, parsley, seashore, pepper, rhubarb, woody, sweet, floral, jasmine, caryophyllene-like, mushroomy, waxy and anisic topnotes are highly desirable in the art of perfumery. Many of the natural materials which provide such fragrances and contribute such desired nuances to perfume compositions as well as perfumed articles are high in cost, unobtainable at times, vary in quality from one batch to another and/or are generally subject to the usual variations of natural products.

There is, accordingly, a continuous effort to find synthetic materials which will replace, enhance or augment the fragrance notes provided by natural essential oils or compositions thereof. Unfortunately, many of the synthetic materials either have the desired nuances only to a relatively small degree or they contribute undesirable or unwanted odor to the perfumes.

Of particular importance are odorants of the minty, herbaceous type for use in fruity and floral fragrances.

Ketals are known for their organoleptic properties, particularly coolant compositions as disclosed and claimed in U.S. Pat. No. 5,451,404 issued on Sep. 19, 1995, the specification for which is incorporated by reference herein. U.S. Pat. No. 5,451,404 discloses coolant compositions to provide cooling sensation to the mucosal membranes and/or to the skin, including toothpastes, mouthwashes, perfumes, lotions, shaving cream, post shaving preparations, shampoos, antiperspirants, deodorants, beverages, chewing gum, tobacco products and pharmaceutical products comprising a ketal and a secondary coolant which may be a menthol, carboxamides or mixtures thereof. The ketals of U.S. Pat. No. 5,451,404 are of the formula:

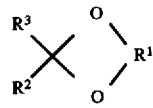

wherein $R^1$ represents a $C_2$–$C_6$ alkylene radical having at least 1 but not more than 3 hydroxyl groups, either $R^2$ and $R^3$ independently of one another represents $C_1$–$C_{10}$ alkyl which is optionally substituted by 1 to 3 radicals selected from the group consisting of hydroxyl, amino and halogen, $C_5$–$C_7$ cycloalkyl, $C_6$–$C_{12}$ aryl, with the proviso that the total number of the C atoms of $R^2$ and $R^3$ is not less than 3, or $R^2$ and $R^3$ together represent an alkylene radical which, together with the carbon atom which carries the radicals $R^2$ and $R^3$, forms a 5-7-membered ring. More specifically, the ketal of U.S. Pat. No. 5,451,404 is preferably of the structure:

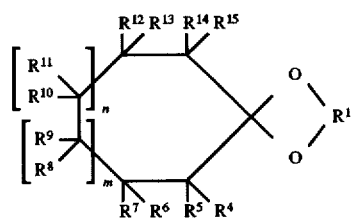

wherein $R^4$ to $R^{15}$ independently of one another denote hydrogen or $C_1$–$C_6$ alkyl, preferably hydrogen or $C_1$–$C_4$ alkyl and m and n independently of one another denote zero or 1. The preferred ketals of U.S. Pat. No. 5,451,404 have the structures:

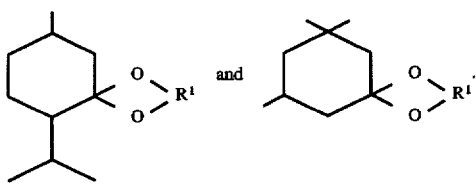

The structures of the ketals of U.S. Pat. No. 5,451,404 are different in kind from the structures of the 7-isopropyl-8,8-dimethyl-6,10-dioxaspiro-$C_{10}$ and $C_{11}$ alkane derivatives of our invention.

Ketals defined according to the structure:

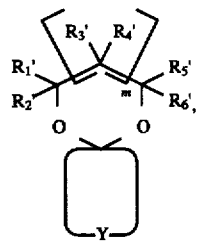

particularly those having the structures:

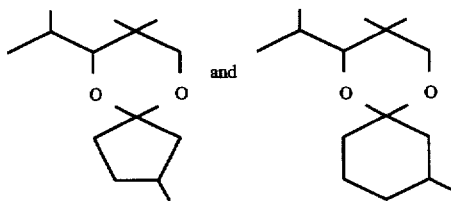

and including the ketals useful in our invention, are indicated in German Offenlegungsschrift No. 2,533,048 published on Feb. 17, 1977 (and abstracted in *Chemical Abstracts*, Volume 86:195071e) to be useful as inflamation preventative agents for cosmetic preparations and for the treatment of sunburn. In the generic structure:

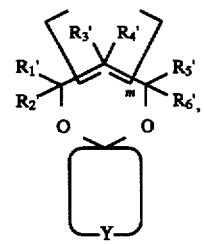

$R_1'$–$R_6'$ represents hydrogen, $C_1$–$C_8$ alkyl or $C_1$–$C_4$ hdyroxyalkyl; m represents zero, 1 or 2; and Y represents, inter alia, alkylene having up to 9 carbon atoms. The German Offenlegungsschrift No. 2,533,048 discloses the use of such compounds as sunburn inhibitors when such compounds are present in such substances as body lotions, shaving lotions, shaving powders and baby powders. German Offenlegungsschrift No. 2,533,048 discloses the use of the compounds having the structure:

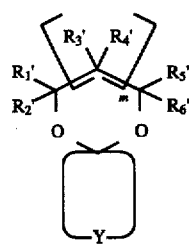

in conjunction with salicylates, for example, benzyl and menthyl salicylate. However, no perfume compositions or perfume bases are indicated to be created using the compounds defined according to the structure:

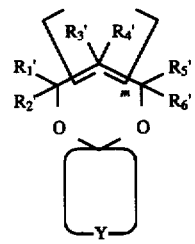

by German Offenlegungsschrift No. 2,533,048. Indeed, German Offenlegungsschrift No. 2,533,048 does not recognize the usefulness in perfumery of the ketals defined according to the generic structure:

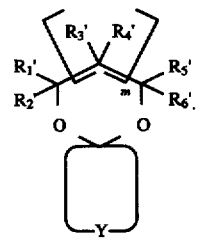

In summary, nothing in the prior art discloses the use of the 7-isopropyl-8,8-dimethyl-6,10-dioxaspiro-$C_{10}$ and $C_{11}$ alkane derivatives of our invention for their perfumery properties.

German Offenlegungsschrift No. 2,533,048 discloses a synthesis for preparing compounds having the structure:

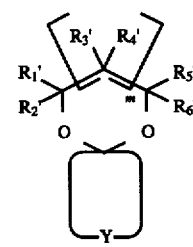

by reacting cycloalkanones with the diols, for example, the diol having the structure:

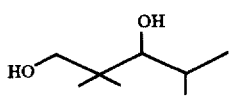

in the presence of triethylorthoformate. However, German Offenlegungsschrift No. 2,533,048 fails to disclose the efficient two step process for preparing substantially pure ketals according to the reactions:

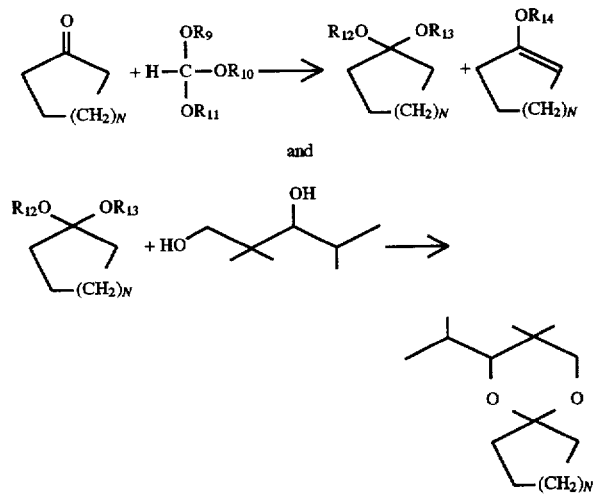

wherein N is 1 or 2; wherein $R_9$, $R_{10}$ and $R_{11}$ are the same or different methyl or ethyl; wherein $R_{12}$ and $R_{13}$ are the same or different methyl or ethyl; and wherein $R_{14}$ is methyl or ethyl.

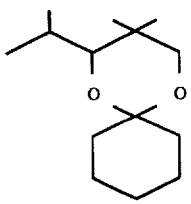

(conditions: SE-30 column programmed from 100°–220° C. at 8° C. per minute).

Figure 2:
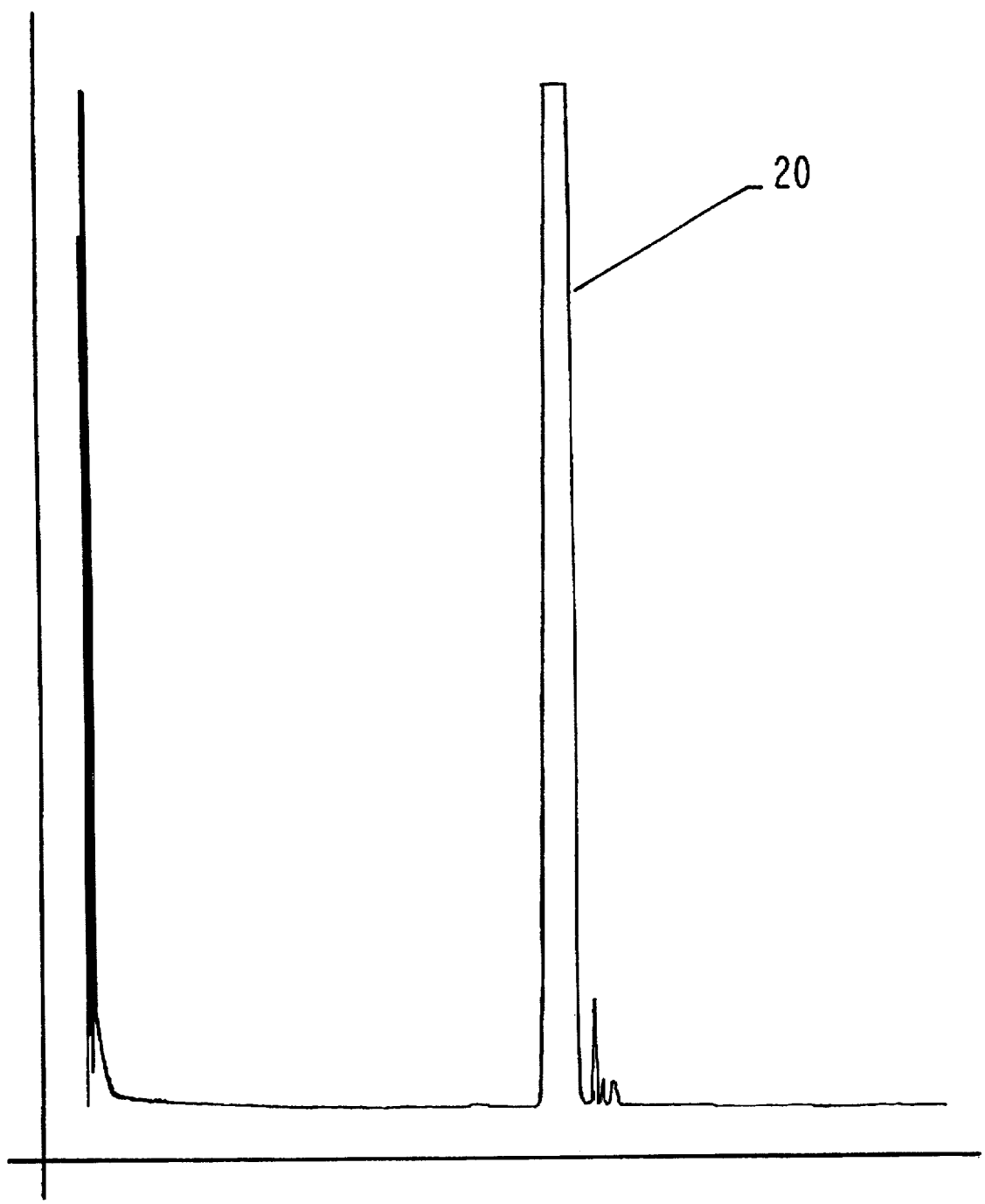

FIG. 2 is the GLC profile for fraction 5 of the distillation product of the reaction product of Example I containing the compound having the structure:

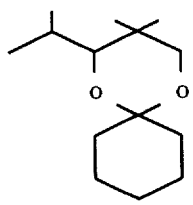

(conditions: SE-30 column programmed from 100°–220° C. at 8° C. per minute).

FIG. 3 is the NMR spectrum for the compound having the struture:

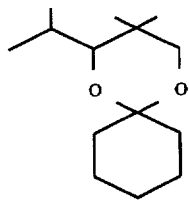

produced according to Example I.

FIG. 3A is an enlargement of section "A" of the GLC profile of FIG. 3.

FIG. 3B is an enlargement of section "B" of the NMR spectrum of FIG. 3.

Figure 4:
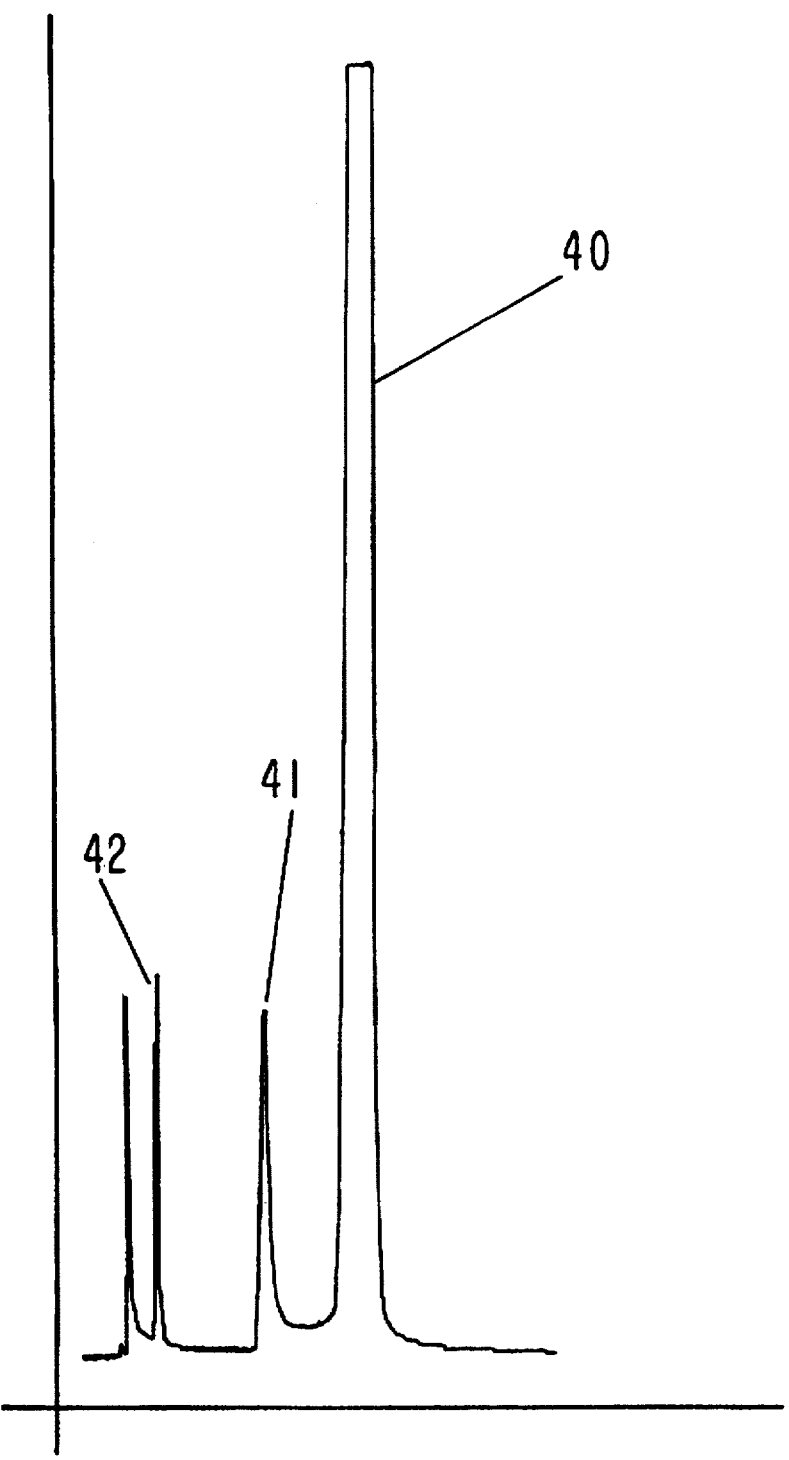

FIG. 4 is the GLC profile of the reaction product of Example II(A) containing the compound having the structure:

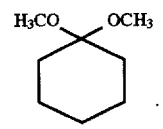

Figure 5:
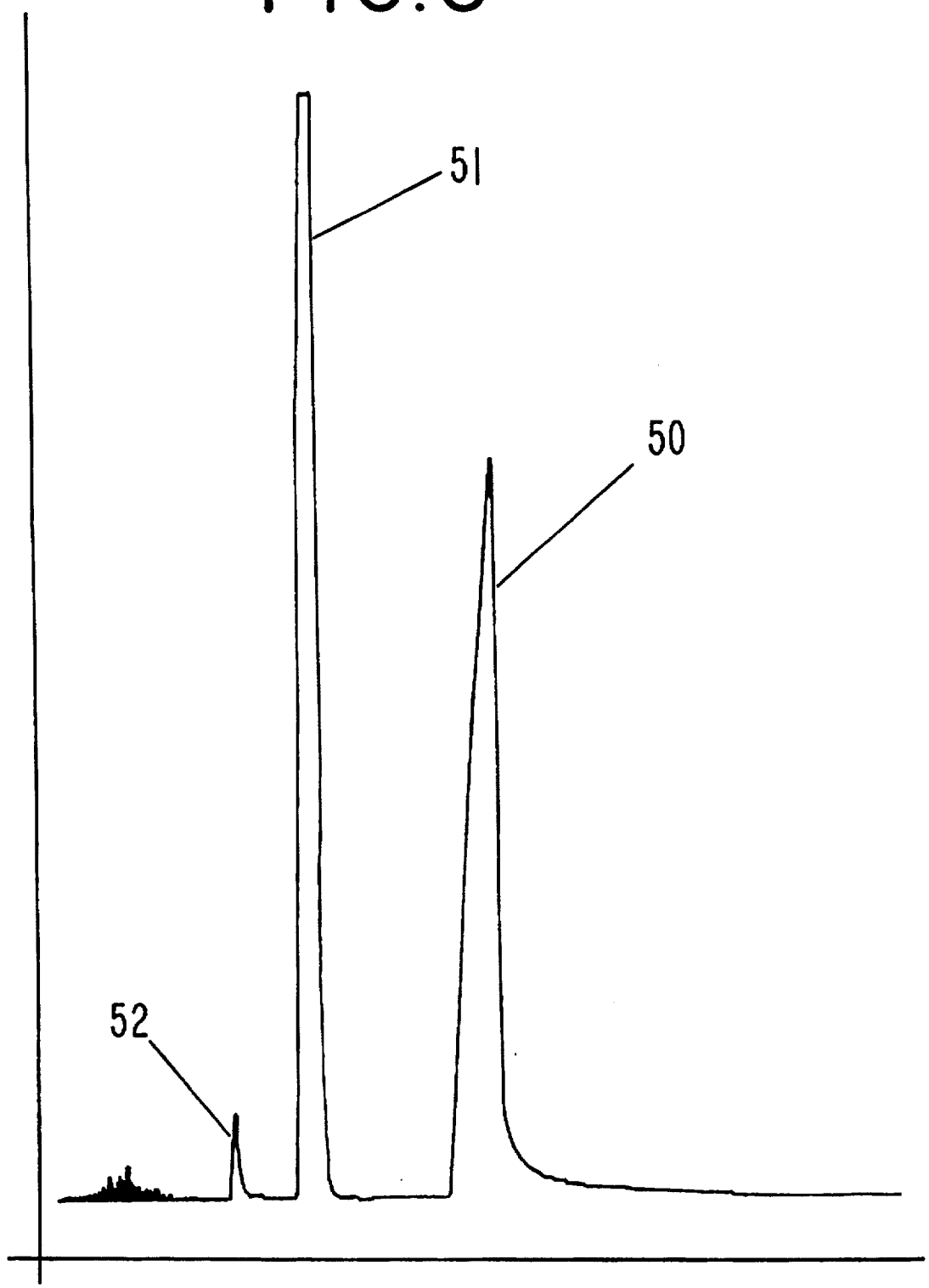

FIG. 5 is a second GLC profile of the reaction product of Example II(A) containing the compound having the structure:

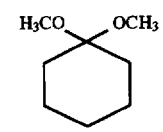

(conditions: SE-30 column programmed from 100°–220° C. at 8° C. per minute).

Figure 6:
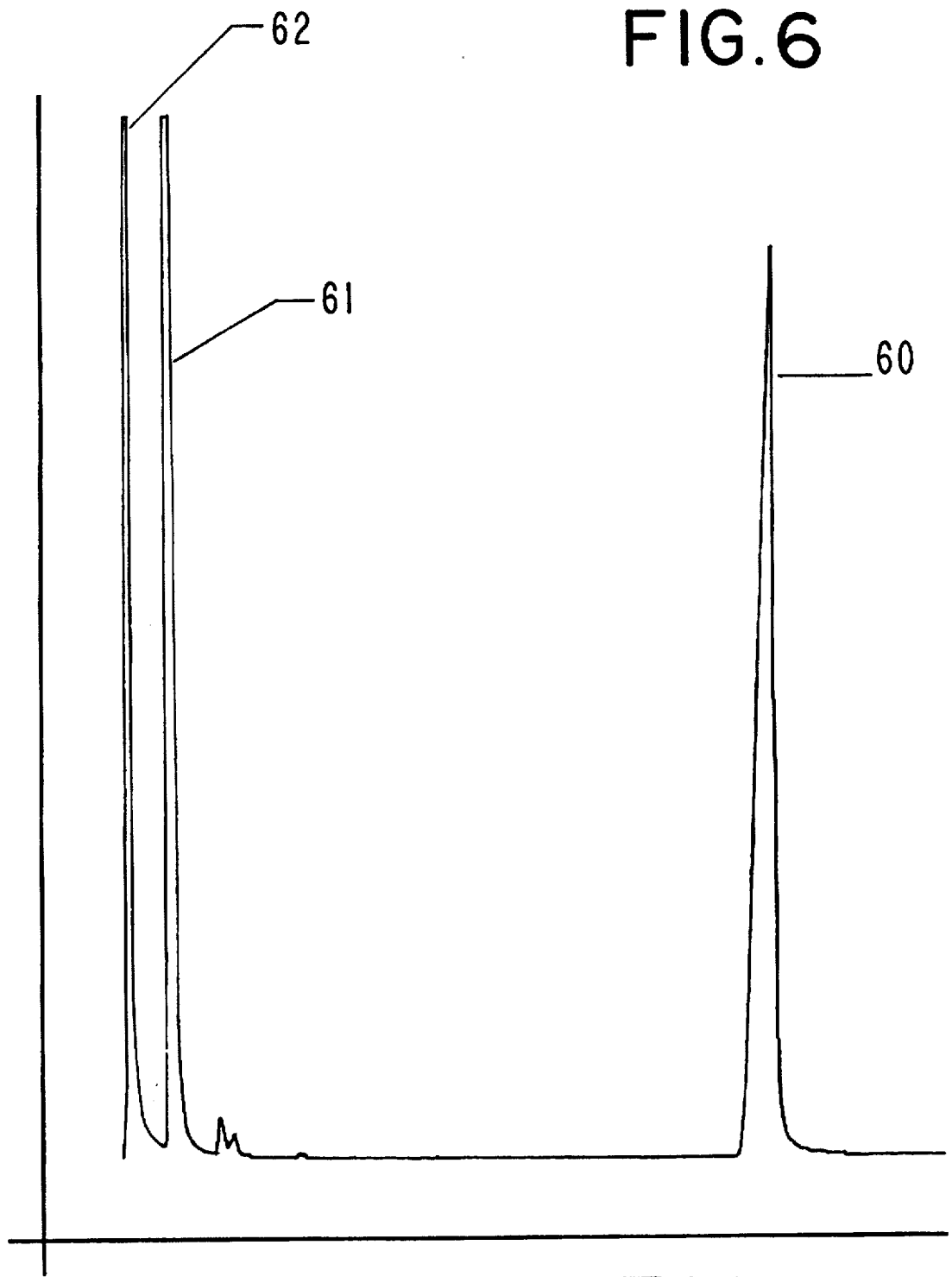

FIG. 6 is the GLC profile for the reaction product of Example II(B) containing the compound having the structure:

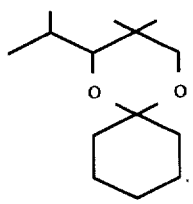

Figure 7:
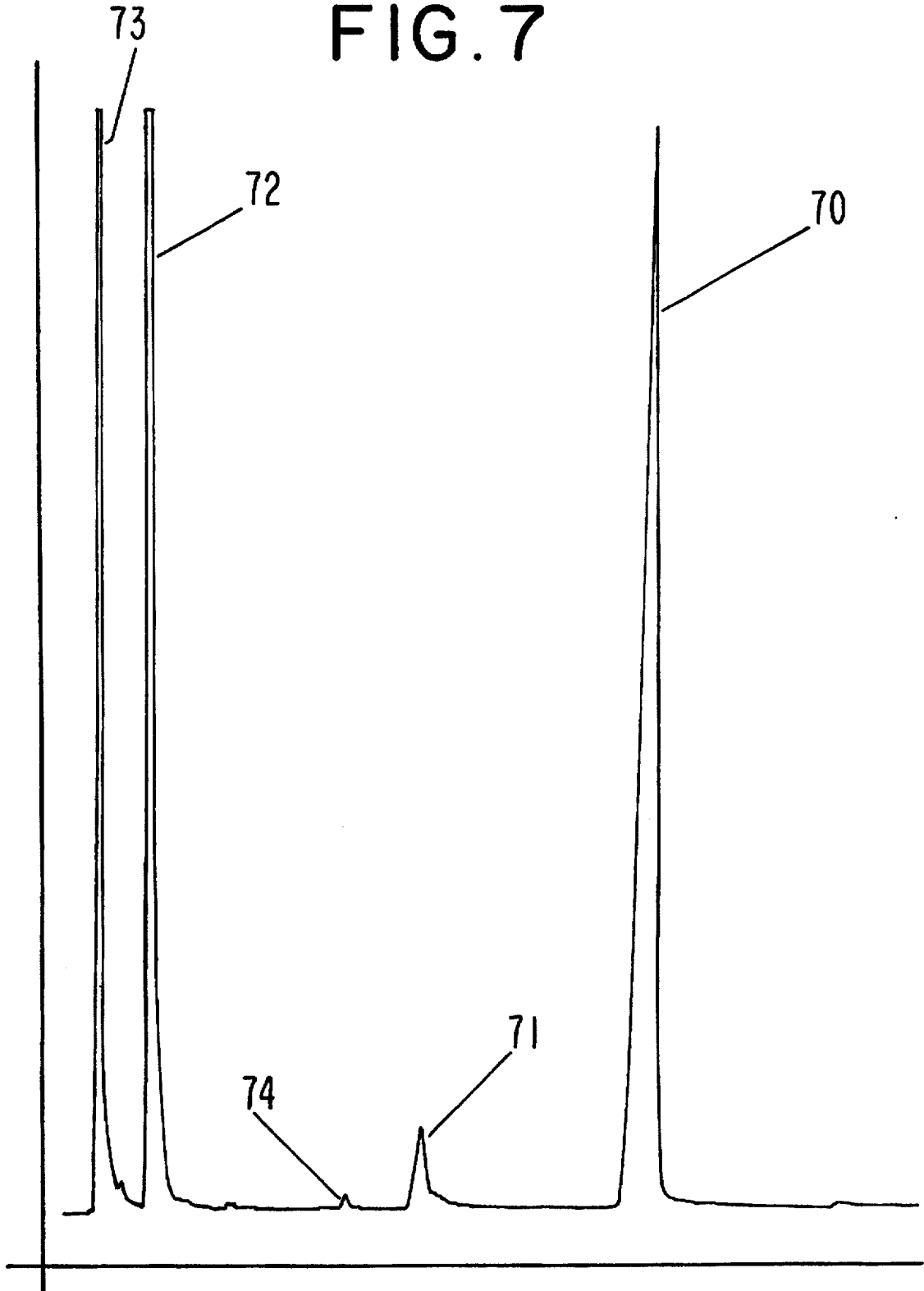

FIG. 7 is the GLC profile of the reaction product of Example III containing the compound having the structure:

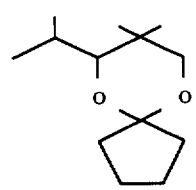

(conditions: SE-30 column programmed from 100°–220° C. at 8° C. per minute).

Figure 8:
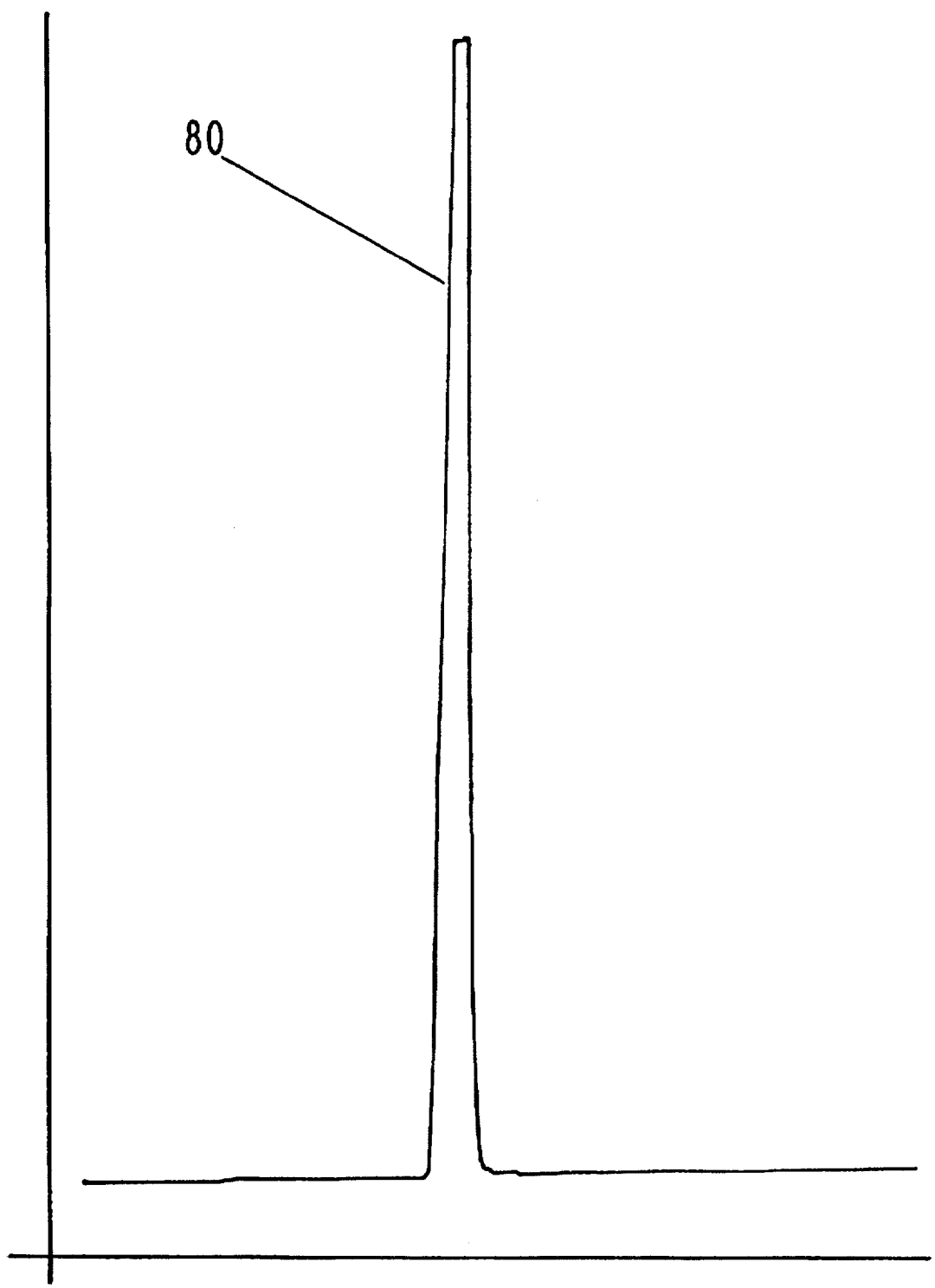

FIG. 8 is the GLC profile of fraction 5 of the distillation of the reaction product of Example III containing the compound having the structure:

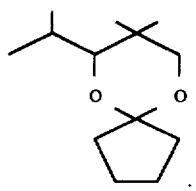

FIG. 9 is the NMR spectrum for the compound having the structure:

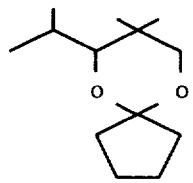

prepared according to Example III.

FIG. 9A is an enlargement of section "A" of the NMR spectrum of FIG. 9.

FIG. 9B is an enlargement of section "B" of the NMR spectrum of FIG. 9.

FIG. 10 is the infrared spectrum of the compound having the structure:

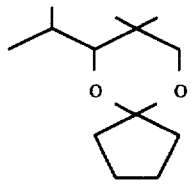

prepared according to Example III.

Figure 11:
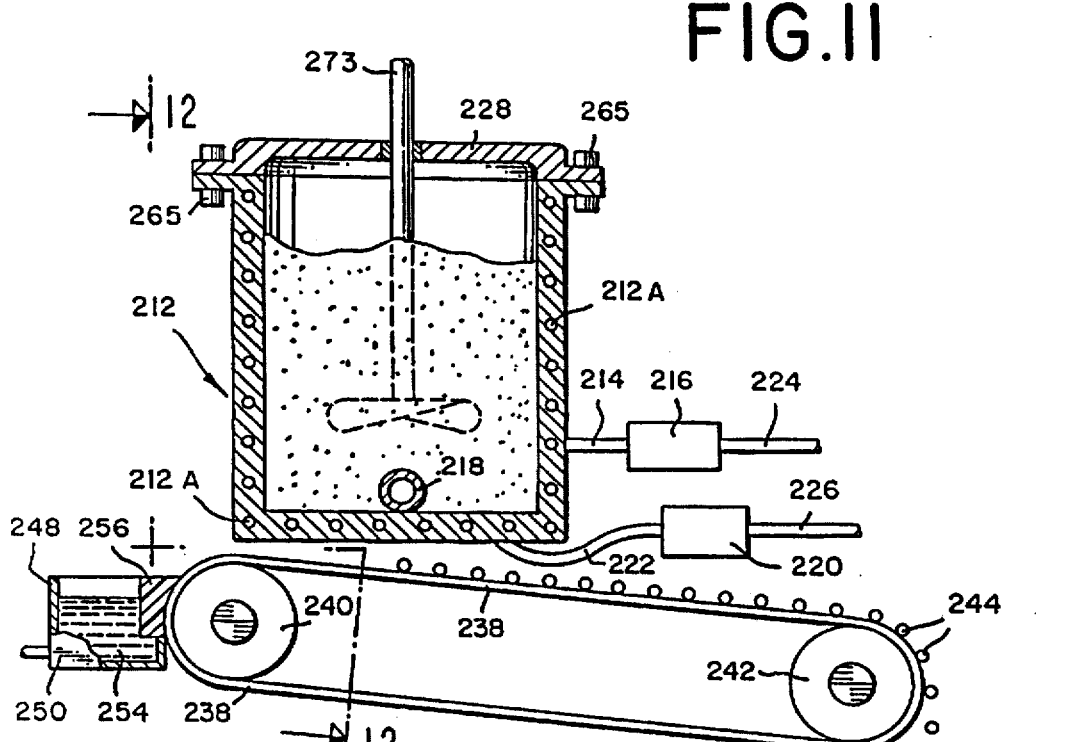

FIG. 11 is a partial side elevation view and partial sectional view an apparatus for forming polymer pellets containing at least one of the 7-isopropyl-8,8-dimethyl-6,10-dioxaspiro-$C_{10}$ and $C_{11}$ alkane derivatives of our invention.

Figure 12:
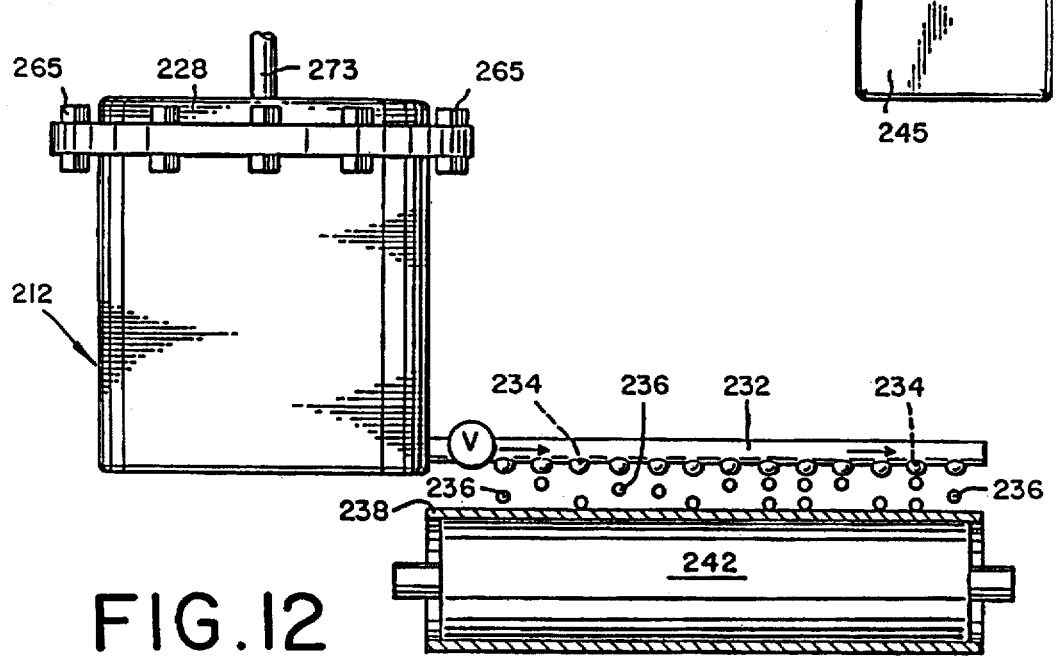

FIG. 12 is a section taken along line 12—12 of FIG. 11.

DETAILED DESCRIPTION OF THE DRAWINGS

Figure 1:
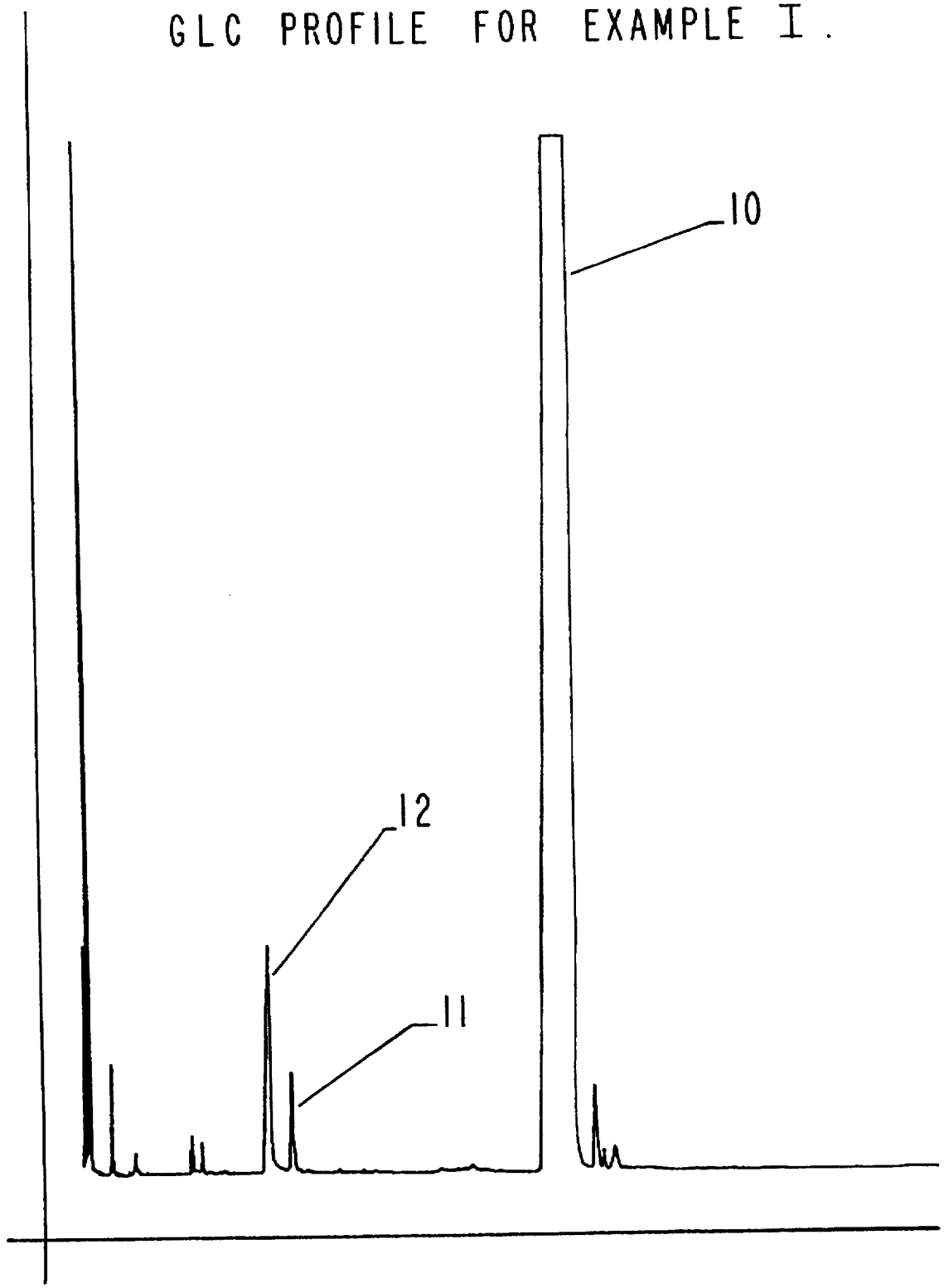
FIG. 1 is the GLC profile for the reaction product of Example I containing the compound having the structure.

Referring to FIG. 1, the peak indicated by reference numeral 10 is the peak for the compound having the structure:

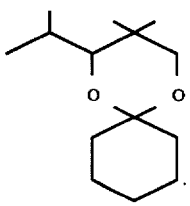

The peak indicated by reference numeral 11 is the peak for the starting material, the diol, having the structure:

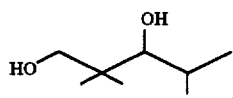

The peak indicated by reference numeral 12 is the peak for the cyclohexanone starting material having the structure:

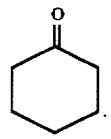

Referring to FIG. 2, the peak indicated by reference numeral 20 is the peak for the compound having the structure:

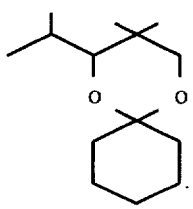

Referring to FIG. 4, the peak indicated by reference numeral 40 is the peak for the ketal having the structure:

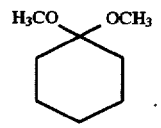

The peak indicated by reference numeral 41 is the peak for the cyclohexanone starting material having the structure:

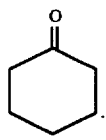

The peak indicated by reference numeral 42 is the peak for the trimethylorthoformate having the structure:

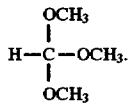

Referring to FIG. 5, the peak indicated by reference numeral 50 is the peak for the diol having the structure:

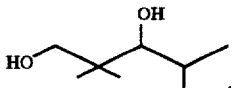

The peak indicated by reference numeral 51 is the peak for the ketal having the structure:

The peak indicated by reference numeral 52 is the peak for the cyclohexanone starting material having the structure:

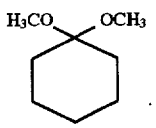

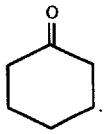

Referring to FIG. 6, the peak indicated by reference numeral 60 is the peak for the compound having the structure:

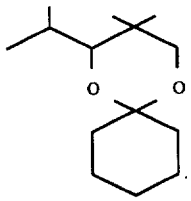

The peak indicated by reference numeral 61 is the peak for the starting material, the glycol, having the structure:

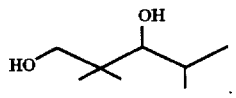

The peak indicated by reference numeral 62 is the peak for the reaction solvent, toluene.

Referring to FIG. 7, the peak indicated by reference numeral 70 is the peak for the compound having the structure:

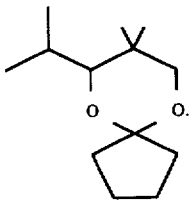

The peak indicated by reference numeral 71 is the peak for the ketal having the structure:

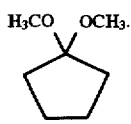

The peak indicated by reference numeral 72 is the peak for the starting material, the glycol, having the structure:

The peak indicated by reference numeral 73 is the peak for the reaction solvent, toluene. The peak indicated by reference numeral 74 is the peak for the cyclopentanone having the structure:

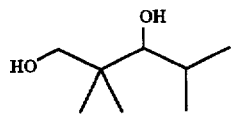

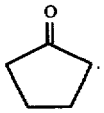

Referring to FIG. 8, the peak indicated by reference numeral 80 is the peak for the product having the structure:

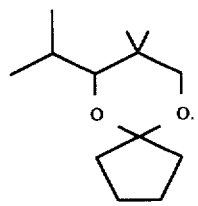

Referring to FIGS. 11 and 12, the apparatus used in producing polymeric fragrances containing one or more of the 7-isopropyl-8,8-dimethyl-6,10-dioxaspiro-$C_{10}$ and $C_{11}$ alkane derivatives of our invention comprises a device for forming scented polyolefin (for example) pellets, which comprises a vat or container 212 into which a mixture of polyolefin such as polyethylene and an aromatic substance or scented material is placed (in this case at least one of the 7-isopropyl-8,8-dimethyl-6,10-dioxaspiro-$C_{10}$ and $C_{11}$ alkane derivatives of our invention).

The container is closed by an air-tight lid 228 and the air-tight lid 228 is clamped to the container 212 by bolts 265.

A stirrer 273 traverses the lid or cover 228 in an air-tight manner and is rotated in a suitable manner.

Container 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless, odorless polymer (e.g., polyethylene) with a viscosity ranging between 180 and 220 Saybolt seconds and having a melting point in the range of 200°–280° F. The heater 212A is operated to maintain the upper portion of the container 212 within a temperature range of from 250°–350° F. The bottom portion of the container is heated by means of heating coils 212A heated through control 220 connected thereto through a connecting wire 222 to maintain the lower portion of the container within a temperature range of from 250°–350° F.

Thus, polymer (e.g., polyethylene is added to container 212 and is heated from 10–12 hours whereafter a scented aroma imparting material (at least one of the 7-isopropyl-8,8-dimethyl-6,10-dioxaspiro-$C_{10}$ and $C_{11}$ alkane derivatives of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally, about 5–30% by weight of the scented material (containing at least one of the 7-isopropyl-8,8-dimethyl-6,10-dioxaspiro-$C_{10}$ and $C_{11}$ alkane derivatives of our invention) are added to the polyolefin.

After the scent imparting material (e.g., a composition containing at least one of the 7-isopropyl-8,8-dimethyl-6,10-dioxaspiro-$C_{10}$ and $C_{11}$ alkane derivatives of our invention) is added to the container 212, the mixture is stirred for a few minutes, for example, 5–15 minutes, and maintained within the temperature range as indicated, supra, by means of heating coils 212A.

The controls 216 and 220 are connected, respectively, through cables 214 and 222, respectively, to heating coils 212A. The said controls 216 and 220 are also connected through cables 224 and 226 respectively, to a suitable power supply of electric current for supplying the electric power to the heating coils 212A for heating purposes.

Thereafter, the valve "V" is opened permitting the mass to flow outwardly through conduit 218/232 having a multiplicity of orifices 234, adjacent to the lower side thereof. The outer end of the conduit 218/232 is closed so that the liquid polymer (e.g., polyolefin) and aroma imparting material (e.g., a mixture containing at least one of the 7-isopropyl-8,8-dimethyl-6,10-dioxaspiro-$C_{10}$ and $C_{11}$ alkane derivatives of our invention) will continuously drop through orifices 234 downwardly from conduit 232. During this time, the temperature of the polymer (e.g., polyolefin) and aroma imparting material (e.g., a mixture containing at least one of the 7-isopropyl-8,8-dimethyl-6,10-dioxaspiro-$C_{10}$ and $C_{11}$ alkane derivatives of our invention) is accurately controlled so that a temperature in the range of from about 210°–275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., one or more of the 7-isopropyl-8,8-dimethyl-6,10-dioxaspiro-$C_{10}$ and $C_{11}$ alkane derivatives of our invention) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 245 and utilized in processes as illustrated, infra.

A feature of this aspect of the process of our invention is the provision for moistening the conveyor belt 238 to insure rapid formation of the solid polymeric (e.g., polyolefin) scented pellets 244 without sticking to the belt. The belt 238 is advantageously fabricated of a material which will not normally stick to a melted plastic, but a moistening means 248 insures a sufficiently cold temperature of the belt surface for an adequate formation of the pellets 244. The adequate moistening means comprises a container 250 which is continuously fed with water 254 to maintain a level for moistening a sponge element 256 which bears against the exterior of the belt 238.

THE INVENTION

The present invention provides 7-isopropyl-8,8-dimethyl-6,10-dioxaspiro-$C_{10}$ and $C_{11}$ alkane derivatives defined according to the generic structure:

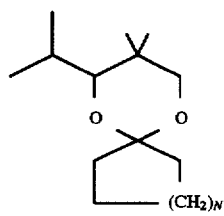

wherein N is 1 or 2 for imparting, augmenting or enhancing the aroma of a substance selected from the group consisting of perfume compositions, perfumed polymers, soaps, anionic, nonionic, cationic or zwitterionic detergents, fabric softener articles, fabric softener compositions and bleach compositions. The present invention also provides perfume compositions consisting essentially of a non-salicylate-containing perfume base and intimately admixed therewith an aroma augmenting or enhancing quantity and concentration of at least one 7-isopropyl-8,8-dimethyl-6,10-dioxaspiro-$C_{10}$ and $C_{11}$ alkane derivative defined according to the structure:

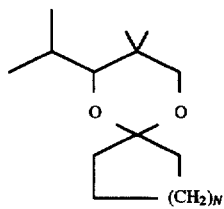

wherein N is 1 or 2. The present invention also provides efficient processes for preparing substantially pure forms of 7-isopropyl-8,8-dimethyl-6,10-dioxaspiro-$C_{10}$ and $C_{11}$ alkane derivatives defined according to the structure:

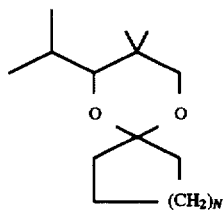

wherein N is 1 or 2 by means of a two step process shown according to the reactions:

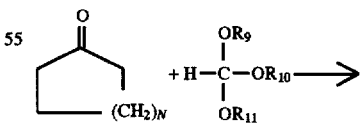

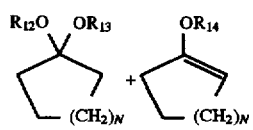

and

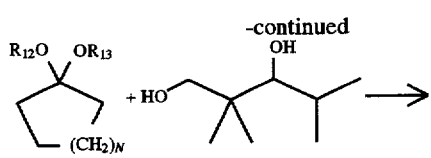

-continued

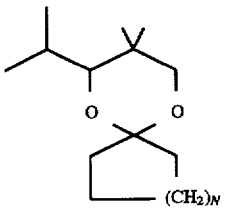

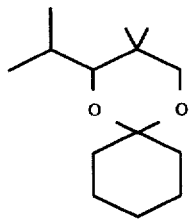

wherein N is 1 or 2; wherein $R_9$, $R_{10}$, $R_{11}$, $R_{12}$ and $R_{13}$ are the same or different methyl or ethyl; and wherein $R_{14}$ is methyl or ethyl.

The compositions of matter of our invention produced according to the processes disclosed in the instant specification are capable of augmenting, enhancing or providing strong, persistent and stable minty, sage, guaiac wood, pepper, fruity, herbal, woody, sweet, balsamic, chamomile, jasmine, eucalyptus and anisic aromas with minty, sage, parsley, seashore, pepper, rhubarb, woody, sweet, floral, jasmine, caryophyllene-like, mushroomy, waxy and anisic topnotes to perfume compositions, colognes and perfumed articles (e.g., solid or liquid, anionic, cationic, nonionic or zwitterionic detergents, fabric softener articles, drier-added fabric softener articles, fabric softener compositions, cosmetic powders, hair preparations, perfumed polymers, alkali metal perborate, bleaches and hypochlorite bleaches).

The 7-isopropyl-8,8-dimethyl-6,10-dioxaspiro-$C_{10}$ and $C_{11}$ alkane derivatives of our invention are known in the prior art, but their perfumery uses are not disclosed or inferred.

Surprisingly and advantageously, the 7-isopropyl-8,8-dimethyl-6,10-dioxaspiro-$C_{10}$ and $C_{11}$ alkane derivatives of our invention are enduring perfume ingredients characterized by their octanol/water partition coefficient (P) being such that their logarithms to the base 10, $\log_{10}P$, are between 4.50 and 5.00. Thus, the $\log_{10}P$ of the compound having the structure:

is 4.65.

It is indicated in U.S. Pat. No. 5,500,137 issued on Mar. 19, 1996, the specification for which is incorporated by reference herein, that a valuable octanol/water partitioning coefficient P of about 1.000 or higher is most advantageous in that it infers an enduring perfume. Indeed, the $\log_{10}P$ of many perfume ingredients has been reported, for example, the POMONA 92® database available from Daylight Chemical Information Systems, Inc. (Daylight CIS), Irvine, Calif., contains many, along with citations to the original literature. The "calculated $\log_{10}P$" is determined by the fragment approach of Hansch and Leo (cf., A. Leo in *Comprehensive Medicinal Chemistry*, Volume 4; C. Hansch, P. G. Sammens, J. B. Taylor and C. A. Ranaden, Editors, page 295, Pergamon Press, 1990, incorporated by reference herein. The fragment approach is based on the chemical structure of each perfume ingredient and takes into account the numbers and types of atoms, the atom connectivity and chemical bonding. The boiling point of the compound having the structure:

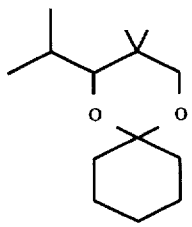

is 83°–84° C. (vapor temperature) at a pressure of 3.0 mm/Hg. The boiling point of the compound having the structure:

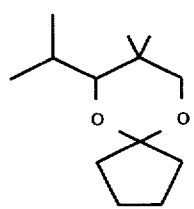

is 87° C. (vapor temperature) at 3.6 mm/Hg. pressure.

It is particularly advantageous that the 7-isopropyl-8,8-dimethyl-6,10-dioxaspiro-$C_{10}$ and $C_{11}$ alkane derivatives defined according to the structure:

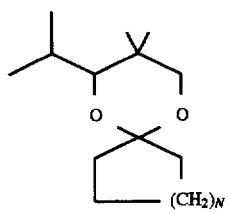

wherein N is 1 or 2 are both "enduring" and, at the same time, bleach stable in hypochlorite bleaches and in alkali metal perborate bleaches.

The 7-isopropyl-8,8-dimethyl-6,10-dioxaspiro-$C_{10}$ and $C_{11}$ alkane derivatives of our invention may be prepared by one of two processes.

Thus, a first process involves the reaction of the diol defined according to the structure:

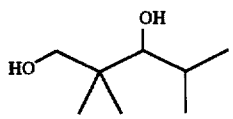

with a cycloalkanone defined according to the structure:

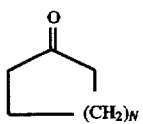

according to the reaction:

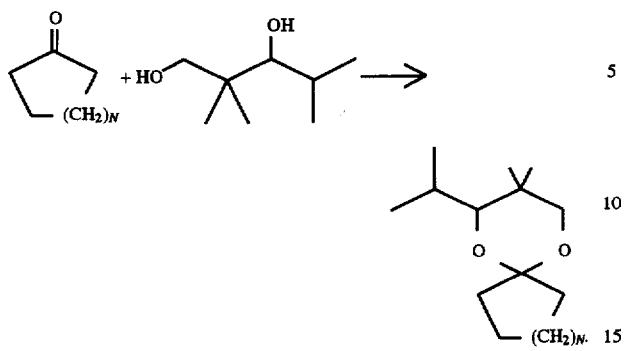

This reaction takes place in the presence of an inert solvent at reflux conditions in the presence of a protonic acid catalyst, preferably paratoluene sulfonic acid or xylene sulfonic acid. The reaction temperature, being at reflux conditions and 1 atmosphere of pressure is about 120° C. The time of reaction is between 3 and about 10 hours. While the reaction is taking place, it is preferable to remove water of reaction, for example, using a Bidwell water trap during the refluxing process.

A second, more preferred (and novel) reaction sequence involves first reacting a cycloalkanone defined according to the structure:

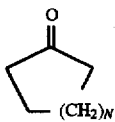

with a trialkylorthoformate having the formula:

$$\begin{array}{c} OR_9 \\ | \\ H-C-OR_{10} \\ | \\ OR_{11} \end{array}$$

wherein $R_9$, $R_{10}$ and $R_{11}$ are the same or different methyl or ehtyl according to the reaction:

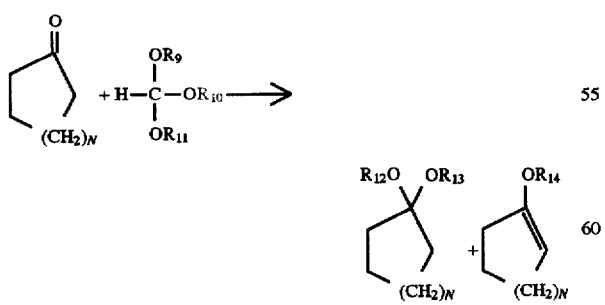

thereby forming a methyl and/or ethyl ketal having the structure:

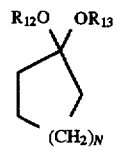

and an enol ether having the structure:

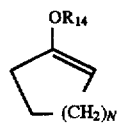

wherein $R_{12}$ and $R_{13}$ are the same or different methyl or ethyl and the structure:

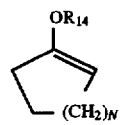

is an individual compound or a mixture in the event that at least one of $R_9$, $R_{10}$ and $R_{11}$ is methyl and at least one of $R_9$, $R_{10}$ and $R_{11}$ is ethyl. This first reaction is carried out at a temperature in the range of from about 35° C. up to about 45° C. at atmospheric pressure in the presence of an inert solvent such as methyl alcohol or ethyl alcohol and a reaction promoter such as acetyl chloride or acetyl bromide. At the end of the reaction, the reaction mass is treated with a small quantity of an alkali metal alkoxide such as sodium methylate or potassium-t-butoxide. Fractional distillation effects the separation of the compound having the structure:

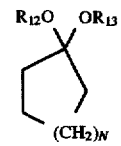

from the compound having the structure:

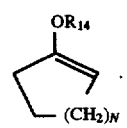

The compound having the structure:

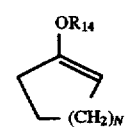

can be used "as is" for its perfumery properties or can be used as a reaction intermediate to form other compounds. The compound having the structure:

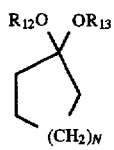

is then further reacted with the diol having the structure:

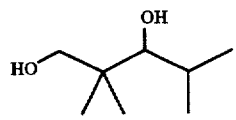

according to the reaction:

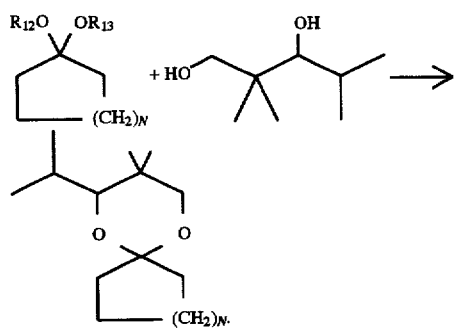

The second reaction of this sequence takes place at reflux conditions in the presence of an inert solvent such as toluene using a catalyst such as paratoluene sulfonic acid. The reaction is carried out at reflux using a Bidwell water trap continuously removing water during the refluxing process. At the end of the reaction, the reaction mass is worked up by neutralizing the reaction mass with, for example, sodium bicarbonate, and then drying the resulting product using anhydrous sodium sulfate. The dried product is then fractionally distilled to yield the substantially pure material defined according to the structure:

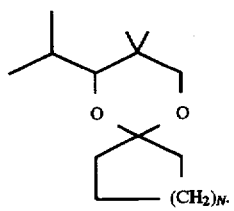

Table I below sets forth the 7-isopropyl-8,8-dimethyl-6,10-dioxaspiro-$C_{10}$ and $C_{11}$ alkane derivatives of our invention and their fragrance properties:

TABLE I

| Structure of Compound | Perfumery Property |
| --- | --- |
| The compound having the structure: | A minty, sage, guaiac wood and pepper aroma with minty, sage, parsley, seashore, pepper, caryophyllene-like and rhubarb topnotes. |

TABLE I-continued

| Structure of Compound | Perfumery Property |
| --- | --- |
| prepared according to Example III, distillation fraction 5. The compound having the structure: | A minty, fruity, herbal, woody, balsamic, chamomile, jasmine, eucalyptus and anisic aroma with woody, sweet, floral, jasmine, mushroomy, waxy and anisic topnotes. |
| prepared according to Example I, bulked distillation fractions 2–4. | |

As olfactory agents, the 7-isopropyl-8,8-dimethyl-6,10-dioxaspiro-$C_{10}$ and $C_{11}$ alkane derivatives of our invention taken alone or in admixture can be formulated into or used as components of a "perfume composition" or can be used as components of a "perfumed article" or the perfume composition may be added to perfumed articles.

The term "perfume composition" is used herein to mean a mixture of organic compounds including, for example, alcohols, aldehydes, ketones, nitriles, ethers, lactones, epoxides, ketals (other than the ketals of our invention), natural essential oils, synthetic essential oils and hydrocarbons which are admixed so that the combined odors of the individual components produce a pleasant or desired fragrance.

With respect to "perfume compositions", it is not intended herein that the perfume compositions of our invention be solely limited to the 7-isopropyl-8,8-dimethyl-6,10-dioxaspiro-$C_{10}$ and $C_{11}$ alkane derivatives of our invention and salicylates such as benzyl salicylate or ethyl salicylate. This invention is not intended to cover compositions solely consisting of salicylates and the 7-isopropyl-8,8-dimethyl-6,10-dioxaspiro-$C_{10}$ and $C_{11}$ alkane derivatives of our invention.

Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation, and substances which retard evaporation; and (d) topnotes which are usually low-boiling, fresh-smelling materials.

In perfume compositions, the individual component will contribute its particular olfactory characteristics, but the overall effect of the perfume composition will be the sum of the effects of each of the ingredients and, in certain instances, a synergistic effect as a result of the addition of certain ingredients. Thus, the individual 7-isopropyl-8,8-dimethyl-6,10-dioxaspiro-$C_{10}$ and $C_{11}$ alkane derivatives of our invention, or mixtures thereof, can be used to alter the aroma characteristics of a perfume composition, for example, by highlighting or moderating the olfactory reaction contributed by another ingredient in the composition.

The amount of the 7-isopropyl-8,8-dimethyl-6,10-dioxaspiro-$C_{10}$ and $C_{11}$ alkane derivatives of this invention which will be effective in perfume compositions depends on many factors including the other ingredients, their amounts and the effects which are desired. It has been found that perfume compositions containing as little as 0.05% of one or both of the 7-isopropyl-8,8-dimethyl-6,10-dioxaspiro-$C_{10}$ and $C_{11}$ alkane derivatives of our invention, or even less, can be used to impart minty, sage, guaiac wood, pepper, fruity, herbal, woody, sweet, balsamic, chamomile, jasmine, eucalyptus and anisic aromas with minty, sage, parsley, seashore, pepper, rhubarb, woody, sweet, floral, jasmine, caryophyllene-like, mushroomy, waxy and anisic topnotes to soaps, solid or liquid, anionic, cationic, nonionic or zwitterionic detergents, cosmetics, cosmetic powders, liquid or solid fabric softeners, drier-added fabric softener articles (e.g., BOUNCE®, a Registered Trademark of the Procter & Gamble Company of Cincinnati, Ohio), optical brightener compositions, hypochlorite bleach compositions, fragranced polymers, hair conditioners and other products. The amount employed can range up to 70% or even higher and will depend on considerations of cost, nature of the end product and the effect desired on the finished product and particular fragrance sought. Thus, for example, when fragrancing liquid bleach compositions containing alkali metal hypochlorite such as, for example, sodium hypochlorite, for example, CLOROX® (Registered Trademark of Clorox, Inc.), the amount employed can range as high as 100% of the fragrance involved in the liquid bleach. Indeed, a distinctive aspect of our invention is the use of one or both of the 7-isopropyl-8,8-dimethyl-6,10-dioxaspiro-$C_{10}$ and $C_{11}$ alkane derivatives of our invention in a stable liquid bleach composition.

The 7-isopropyl-8,8-dimethyl-6,10-dioxaspiro-$C_{10}$ and $C_{11}$ alkane derivatives of our invention, taken alone or in admixture, can be used alone or in a perfume composition (in the absence of a salicylates such as benzyl salicylate or menthyl salicylate) as an olfactory component in detergents, soaps, space odorants and deodorants; perfumes; colognes, toilet waters; bath salts; hair preparations such as lacquers, brilliantines, pomades and shampoos; cosmetic preparations such as creams, deodorants, hand lotions, such as creams; powders such as talcs, dusting powders, face powders and the like; liquid bleaches such as sodium hypochlorite-containing bleaches; floor waxes, automobile aromas and automobile polish compositions.

When used as an olfactory component of a perfumed article, as little as 0.01% of one or both of the 7-isopropyl-8,8-dimethyl-6,10-dioxaspiro-$C_{10}$ and $C_{11}$ alkane derivatives of our invention will suffice to impart an interesting minty, sage, guaiac wood, pepper, fruity, herbal, woody, sweet, balsamic, chamomile, jasmine, eucalyptus and anisic aromas with minty, sage, parsley, seashore, pepper, rhubarb, woody, sweet, floral, jasmine, caryophyllene-like, mushroomy, waxy and anisic topnotes. Generally, no more than 1.5% is required to impart such aromas. However, in view of the rather low cost of the 7-isopropyl-8,8-dimethyl-6,10-dioxaspiro-$C_{10}$ and $C_{11}$ alkane derivatives of our invention, up to 100% of the perfume composition can be one or both of the 7-isopropyl-8,8-dimethyl-6,10-dioxaspiro-$C_{10}$ and $C_{11}$ alkane derivatives of our invention.

In summary, the range of the 7-isopropyl-8,8-dimethyl-6,10-dioxaspiro-$C_{10}$ and $C_{11}$ alkane derivatives of our invention in the perfumed article can be from 0.01% up to 1.5% or even higher.

In addition, the perfume composition of our invention can contain a vehicle or carrier for the 7-isopropyl-8,8-dimethyl-6,10-dioxaspiro-$C_{10}$ and $C_{11}$ alkane derivatives of our invention, taken alone or with other ingredients. The vehicle can be a liquid such as a non-toxic alcohol such as ethanol, a glycol such as propylene glycol or the like. The carrier can be an absorbent solid such as a gum or components for encapsulating the composition such as gelatin which can be used to form a capsule wall surrounding the perfume oil as by means of coacervation with gelatin or as by means of formation of a polymer around the perfume oil as by polymerizing a urea formaldehyde prepolymer.

It will thus be apparent that the 7-isopropyl-8,8-dimethyl-6,10-dioxaspiro-$C_{10}$ and $C_{11}$ alkane derivatives of our invention can be used to alter, modify, augment or enhance sensory properties, particularly organoleptic properties such as fragrances of a wide variety of consumable materials.

The 7-isopropyl-8,8-dimethyl-6,10-dioxaspiro-$C_{10}$ and $C_{11}$ alkane derivatives of our invention defined according to the structure:

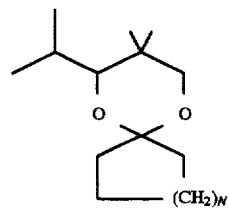

wherein N is 1 or 2 are also useful in conjunction with bleaches which are "per-bleaches", for example, sodium perborate, sodium percarbonate or sodium persulfate. More particularly, the 7-isopropyl-8,8-dimethyl-6,10-dioxaspiro-$C_{10}$ and $C_{11}$ alkane derivatives of our invention are useful in conjunction with particulate bleach activator compositions for per-bleaches as more specifically described in U.S. Pat. No. 5,534,195 issued on Jul. 9, 1996, the specification for which is incorporated by reference herein.

The 7-isopropyl-8,8-dimethyl-6,10-dioxaspiro-$C_{10}$ and $C_{11}$ alkane derivatives of our invention may be combined with lactam bleach activator-containing particles which are specifically described in U.S. Pat. No. 5,534,196 issued on Jul. 9, 1996, the specification for which is incorporated by reference herein.

PCT Application Ser. No. 95/07972 (corresponding to Czech Republic Application No. 96/00774) may be also utilized in conjunction with the 7-isopropyl-8,8-dimethyl-6,10-dioxaspiro-$C_{10}$ and $C_{11}$ alkane derivatives of our invention defined according to the structure:

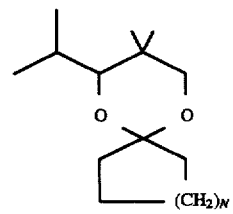

wherein N is 1 or 2. Thus, the compound having the structure:

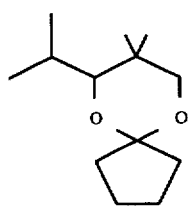

may be combined in an amount of between 2 and 4% by weight in a bleach composition for a detergent comprising enzymatic hydrogen peroxide-generating system and coordination complex containing manganese ions as a bleach catalyst; or a coordination complex containing ferric ions as a bleach catalyst; or a coordination complex containing $Mn^{++}$ (50%) and $Fe^{++}$ ions as a bleach catalyst.

The 7-isopropyl-8,8-dimethyl-6,10-dioxaspiro-$C_{10}$ and $C_{11}$ alkane derivatives of our invention defined according to the structure:

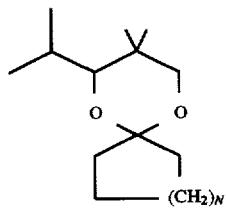

may also be used in sodium percarbonate particles used for bleaching wherein the particles have the external surfaces thereof coated with sodium borate as described in Spanish Patent Application No. 2,085,971 (Kao Corporation) corresponding to European Patent No. 487,256.

The 7-isopropyl-8,8-dimethyl-6,10-dioxaspiro-$C_{10}$ and $C_{11}$ alkane derivatives of our invention defined according to the structure:

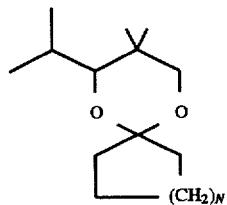

wherein N is 1 or 2 are also useful in imparting aromas to bleach detergent compositions containing acid-based bleaching based compounds which generate hydrogen peroxide and which also include bleaching activators, cellulase and silicon compounds, for example, Japanese Published Patent Application No. JP08/157881 (Lion Corporation), which covers the combined use of the specific bleaching activator having the structure:

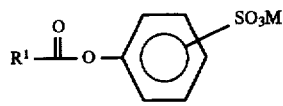

or having the structure:

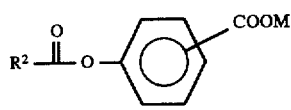

wherein $R^1$ is $C_{10}$–$C_{18}$ alkyl or alkenyl; $R^2$ is $C_7$–$C_{18}$ alkyl or alkenyl; and M represents a cation for providing water solubility to the bleaching activator, for example, M is sodium or potassium. The amount of 7-isopropyl-8,8-dimethyl-6,10-dioxaspiro-$C_{10}$ and $C_{11}$ alkane derivative of our invention defined according to the structure:

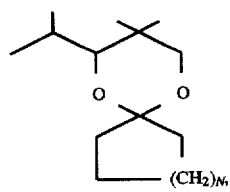

for example, the compound having the structure:

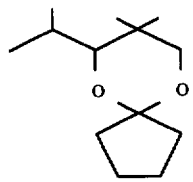

is used in such bleaching detergent compositions in an amount of from about 2% up to about 4%. A specific example is one containing 2% of the compound having the structure:

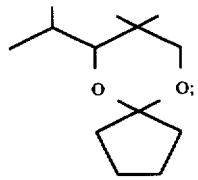

an acid-based bleaching based composition compound generating hydrogen peroxide and water; 0.5 weight percent cellulase; and 0.5 weight percent of a silicon compound. The 7-isopropyl-8,8-dimethyl-6,10-dioxaspiro-$C_{10}$ and $C_{11}$ alkane derivatives of our invention can also be used in bleaching detergent compositions described in Published Japanese Applications as follows:

JP08/157874;
JP08/157876;
JP08/157877;
JP08/157878;
JP08/157880;
JP08/157882;
JP08/157883;
JP08/157889; and
JP08/157890.

The 7-isopropyl-8,8-dimethyl-6,10-dioxaspiro-$C_{10}$ and $C_{11}$ alkane derivatives of our invention defined according to the structure:

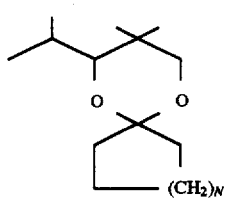

wherein N is 1 or 2 are also useful in bleach compositions when admixed with the non-friable composite granule bleach catalysts described in U.S. Pat. No. 5,536,441 issued on Jul. 16, 1996, the specification for which is incorporated by reference herein. In U.S. Pat. No. 5,536,441, described is a non-friable composite granule bleach composition containing mono- or di-nuclear manganese complex catalysts with amine ligands and soluble binding agents.

The following examples serve to illustrate our invention, and this invention is considered to be restricted thereto only as indicated in the appended claims.

All parts and percentages given herein are by weight unless otherwise specified.

EXAMPLE I

PREPARATION OF

7-ISOPROPYL-8,8-DIMETHYL-6,10-DIOXASPIROCYCLOHEXANE

Reaction:

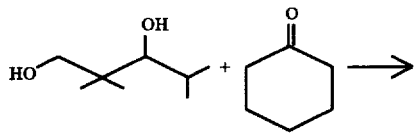

Into a 5 liter reaction vessel equipped with stirrer, thermometer, reflux condenser, heating mantle and Bidwell trap are placed the following materials:

(i) 2,2,4-trimethylpentane-1,3-diol having the structure:

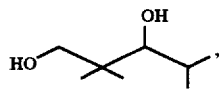

6.85 moles;

(ii) cyclohexanone, 6.22 moles;

(iii) toluene, 5.43 moles; and (iv) paratoluene sulfonic acid, 0.58 moles.

The resulting mixture with stirring is heated to reflux and refluxed at 120° C. for a period of 5 hours.

At the end of the 5 hour period, the resulting reaction mass is washed with two 500 ml volumes of 10% aqueous sodium bicarbonate solution followed by 1 volume of saturated aqueous sodium chloride solution. The resulting product now exists in two phases: an aqueous phase and an organic phase. The aqueous phase is separated from the organic phase, and the organic phase is distilled on a two inch splash ("rushover") distillation column yielding the following fractions:

| Fraction Number | Vapor Temperature (°C.) | Liquid Temperature (°C.) | Vacuum mm/Hg. Pressure |
|---|---|---|---|
| 1 | 40 | 80 | 200.0 |
| 2 | 28 | 82 | 30.0 |
| 3 | 74 | 113 | 2.0 |
| 4 | 87 | 125 | 1.5 |
| 5 | 35 | 137 | 3.0 |

Fractions 3–5 are bulked and redistilled on a 2 foot Goodloe distillation column yielding the following fractions:

| Fraction Number | Vapor Temperature (°C.) | Liquid Temperature (°C.) | Vacuum mm/Hg. Pressure |
|---|---|---|---|
| 1 | 41/78 | 118/132 | 3.0 |
| 2 | 78 | 131 | 3.0 |
| 3 | 83 | 135 | 3.0 |
| 4 | 84 | 134 | 3.0 |
| 5 | 84 | 133 | 3.0 |

Fractions 2–4 are bulked for fragrance use and for use in Examples IV, et seq. Bulked distillation fractions 2–4 have a minty, fruity, herbal, woody, sweet, balsamic, chamomile, jasmine, eucalyptus and anisic aroma with woody, sweet, floral, jasmine, mushroomy, waxy and anisic topnotes. Bulked distillation fractions 2–4 consist of the compound having the structure:

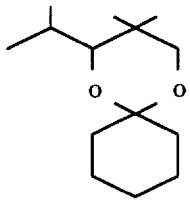

as confirmed by NMR, IR, mass spectral and GLC analyses.

EXAMPLE II

PREPARATION OF

7-ISOPROPYL-8,8-DIMETHYL-6,10-DIOXASPIROCYCLOHEXANE

EXAMPLE II (A)

STEP 1

Reaction:

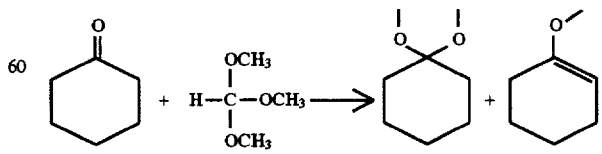

Into a 3 liter reaction flask equipped with stirrer, thermometer, reflux condenser and heating mantle are placed the following materials:

(i) cyclohexanone, 5.1 moles;

(ii) trimethylorthoformate, 5.66 moles; and (iii) methanol, 15.63 moles.

The resulting mixture is heated to 35° C. and over a period of 1 hour, 19 moles of acetyl chloride is added to the reaction mass while the reaction mass temperature with stirring is at 40°–45° C. During the addition of the acetyl chloride, methyl formate is distilled from the reaction mass.

At the end of the feeding of the acetyl chloride, the reaction mass is cooled to 40° C. Over a period of 1 hour, 40 grams of sodium methylate is added to the reaction mass.

The reaction mass is then fractionally distilled on a two inch splash column yielding the following fractions:

| Fraction Number | Vapor Temperature (°C.) | Liquid Temperature (°C.) | Vacuum mm/Hg. Pressure |
|---|---|---|---|
| 1 | 26/40 | 66/77 | 75 |
| 2 | 51 | 66 | 75 |
| 3 | 50 | 63 | 75 |
| 4 | 48 | 73 | 75 |
| 5 | 41 | 112 | 75 |

Fractions 2, 3 and 4 are bulked for the subsequent reaction in Example II(B). Bulked distillation fractions 2–4 consist of the compound having the structure:

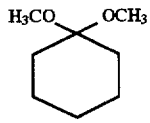

as confirmed by NMR, GLC, mass spectral and IR analyses.

EXAMPLE II (B)

STEP 2

Reaction:

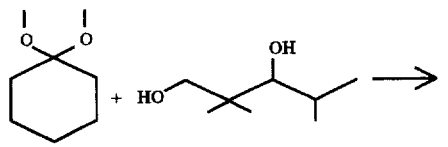

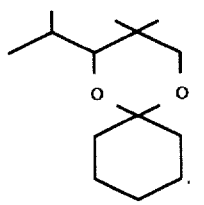

Into a 2 liter reaction vessel equipped with stirrer, thermometer, reflux condenser, heating mantle and a Bidwell water trap are placed the following materials:

(i) 2,2,4-trimethylpentane-1,3-diol having the structure:

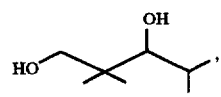

2.05 moles;

(ii) cyclohexanone dimethylketal having the structure:

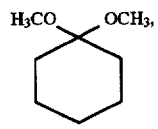

2.08 moles;

(iii) toluene, 5.43 moles; and (iv) paratoluene sulfonic acid, 0.06 moles (11 grams).

The resulting mixture is heated to reflux and refluxed at a temperature of 170° C. for a period of 2 hours. At the end of the 2 hour period, 36 ml water was collected.

The resulting reaction mass is washed with an equal volume of 10% aqueous sodium bicarbonate. The aqueous phase is separated from the organic phase, and the organic phase is dried over anhydrous sodium sulfate. The resulting dried product is then fractionally distilled on a two inch splash column yielding the following fractions:

| Fraction Number | Vapor Temperature (°C.) | Liquid Temperature (°C.) | Vacuum mm/Hg. Pressure |
|---|---|---|---|
| 1 | 26/87 | 47/105 | 2.0 |
| 2 | 106 | 109 | 3.4 |
| 3 | 51 | 131 | 3.8 |

Fraction 2 consists of a compound having the structure:

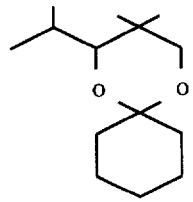

as confirmed by NMR, IR and mass spectral analyses.

Fraction 2 has a minty, fruity, herbal, woody, sweet, balsamic, chamomile, jasmine, eucalyptus, anisic and earthy aroma with woody, sweet, floral, jasmine, mushroomy, waxy and anisic topnotes.

EXAMPLE III

PREPARATION OF

7-ISOPROPYL-8,8-DIMETHYL-6,10-DIOXASPIROCYCLOPENTANONE

Reactions:

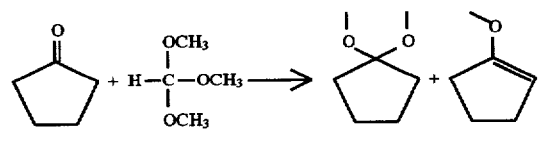

and

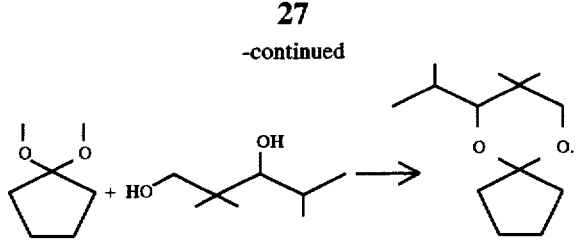

Into a 2 liter reaction vessel equipped with stirrer, thermometer, reflux condenser, heating mantle and Bidwell trap are placed the following materials:
(i) 2,2,4-trimethylpentane-1,3-diol having the structure:

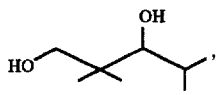

2.05 moles;
(ii) cyclopentanone dimethylketal having the structure:

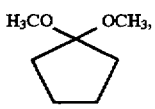

1.92 moles;
(iii) toluene, 5.43 moles; and
(iv) paratoluene sulfonic acid, 0.06 moles.
The compound having the structure:

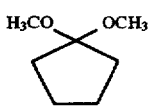

is previously prepared according to the reaction:

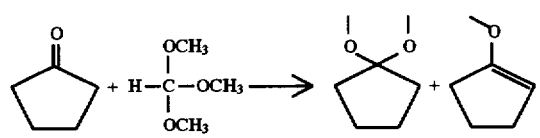

and the compound having the structure:

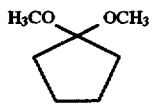

is separated by fractional distillation from the previously formed 1-methoxycyclopentene.

The mixture in the 2 liter reaction vessel is heated to reflux with stirring and refluxed at a temperature of 190° C. for a period of 3 hours while removing water using the Bidwell trap. 36 Ml water is removed.

The reaction mass is then cooled to room temperature and washed with an equal volume of 10% aqueous sodium bicarbonate solution, followed by an equal volume of aqueous 10% sodium chloride solution.

The organic phase is then separated from the aqueous phase, and the organic phase is dried using anhydrous sodium sulfate.

The resulting product is then fractionally distilled yielding the following fractions:

| Fraction Number | Vapor Temperature (°C.) | Liquid Temperature (°C.) | Vacuum mm/Hg. Pressure |
|---|---|---|---|
| 1 | 31 | 50 | 250 |
| 2 | 28 | 56 | 20 |
| 3 | 77 | 95 | 4 |
| 4 | 87 | 98 | 3.6 |
| 5 | 79 | 145 | 3.4 |

Fraction 5 consists of the compound having the structure:

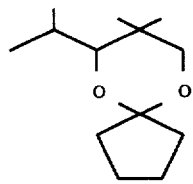

as confirmed by NMR, IR, mass spectral and GLC analyses.
The compound having the structure:

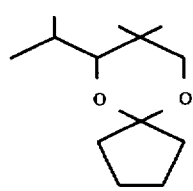

has a minty, sage, guaiac wood and pepper aroma with minty, sage, parsley, seashore, pepper, caryophyllene-like and rhubarb topnotes.

EXAMPLE IV

PERFUME FORMULATIONS

The following floral, woody cologne perfume formulations are prepared:

| Ingredients | Parts by Weight | | |
|---|---|---|---|
| | IV(A) | IV(B) | IV(C) |
| Phenyl ethyl alcohol | 200 | 200 | 200 |
| Bergamot oil | 150 | 150 | 150 |
| Orange oil | 200 | 200 | 200 |
| Lemon oil | 50 | 50 | 50 |
| Eugenol | 10 | 10 | 10 |
| 4-(4-methyl-4-hydroxy amyl)-$\Delta^3$ cyclohexane carboxaldehyde (LYRAL ®, Trademark of International Flavors & Fragrances Inc. of New York, New York) | 40 | 40 | 40 |
| Ylang oil | 2 | 2 | 2 |
| Petigrain Paraguay | 10 | 10 | 10 |
| γ-Methyl ionone | 20 | 20 | 20 |
| Vetiver Venezuela | 18 | 18 | 18 |
| 3-α-Methyl-dodecahydro-6,6,9a-trimethyl-naphthol [2.1-b] furan | 5 | 5 | 5 |
| Product produced by the reaction of acetic anhydride, polyphosphoric acid and 1,5,9-trimethyl cyclododecatriene-1,5,9 according to the process of Example I of U.S. Pat. No. 3,718,698, the specification for which is incorporated by reference herein. | 50 | 50 | 50 |
| Octahydro-9,9-dimethyl-1,6-methano-naphthalene-1-[2H]-ol produced according to Example III of U.S. Pat. No. 3,996,169, the specification for which is incorporated by | 50 | 50 | 50 |

-continued

| Ingredients | Parts by Weight | | |
|---|---|---|---|
| | IV(A) | IV(B) | IV(C) | reference herein.
The compound having the structure: 25 0 25

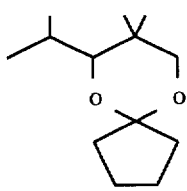

prepared according to Example III,
distillation fraction 5.
The compound having the structure: 0 25 25

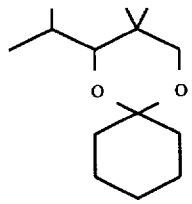

prepared according to Example I,
distillation fractions 2-4.

The compound having the structure:

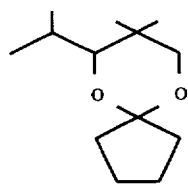

prepared according to Example III, distillation fraction 5, imparts to this floral, woody cologne formulation strong, persistent minty, sage, guaiac wood and pepper undertones with minty, sage, parsley, seashore, pepper, caryophyllene-like and rhubarb topnotes. Accordingly, the perfume composition of Example IV(A) is described as:

"A floral, woody cologne aroma with strong, persistent minty, sage, guaiac wood and pepper undertones and minty, sage, parsley, seashore, pepper, caryophyllene-like and rhubarb topnotes."

The compound having the structure:

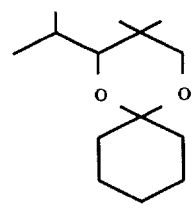

prepared according to Example I, bulked distillation fractions 2-4, imparts to this floral, woody cologne formulation strong, persistent minty, fruity, herbal, woody, sweet, balsamic, chamomile, jasmine, eucalyptus and anisic undertones with woody, sweet, floral, jasmine, mushroomy, waxy and anisic topnotes. Accordingly, the perfume composition of Example IV(B) is described as:

"A floral, woody cologne aroma with strong, persistent minty, fruity, herbal, woody, sweet, balsamic, chamomile, jasmine, eucalyptus and anisic undertones and woody, sweet, floral, jasmine, mushroomy, waxy and anisic topnotes."

The combination of the compounds having the structures:

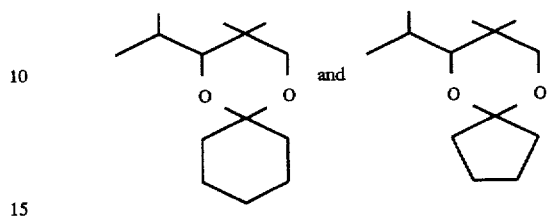

imparts to this floral, woody cologne formulation strong, persistent minty, sage, guaiac wood, pepper, fruity, herbal, woody, sweet, balsamic, chamomile, jasmine, eucalyptus and anisic undertones with minty, sage, parsley, seashore, pepper, rhubarb, woody, sweet, floral, jasmine, caryophyllene-like, mushroomy, waxy and anisic topnotes. Accordingly, the perfume composition of Example IV(C) is described as:

"A floral, woody cologne aroma with strong, persistent minty, sage, guaiac wood, pepper, fruity, herbal, woody, sweet, balsamic, chamomile, jasmine, eucalyptus and anisic undertones with minty, sage, parsley, seashore, pepper, rhubarb, woody, sweet, floral, jasmine, caryophyllene-like, mushroomy, waxy and anisic topnotes."

EXAMPLE V

PREPARATION OF COSMETIC POWDER COMPOSITION

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| The compound having the structure: | A minty, sage, guaiac wood and pepper aroma with minty, sage, parsley, seashore, pepper, caryophyllene-like and rhubarb topnotes. |

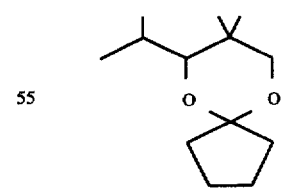

prepared according to Example III,
supra, distillation fraction 5.

| The compound having the structure: | A minty, fruity, herbal, woody, sweet, balsamic, chamomile, jasmine, eucalyptus and anisic aroma with woody, sweet, floral, jasmine, mushroomy, waxy and anisic topnotes. |

TABLE II-continued

| Substance | Aroma Description |
|---|---|
| prepared according to Example I, supra, bulked distillation fractions 2-4. The compound having the structure: [structure] | A minty, fruity, herbal, woody, sweet, balsamic, chamomile, jasmine, eucalyptus, anisic and earthy aroma with woody, sweet, floral, jasmine, mushroomy, waxy and anisic topnotes. |
| prepared according Example II (B), bulked distillation fractions 2-4. [structure] | |
| The perfume composition of Example IV(A). | A floral, woody cologne aroma with strong, persistent minty, sage, guaiac wood and pepper undertones and minty, sage, parsley, seashore, pepper, caryophyllene-like and rhubarb topnotes. |
| The perfume composition of Example IV(B). | A floral, woody cologne aroma with strong, persistent minty, fruity, herbal, woody, sweet, balsamic, chamomile, jasmine, eucalyptus and anisic undertones and woody, sweet, floral, jasmine, mushroomy, waxy and anisic topnotes. |
| The perfume composition of Example IV(C). | A floral, woody cologne aroma with strong, persistent minty, sage, guaiac wood, pepper, fruity, herbal, woody, sweet, balsamic, chamomile, jasmine, eucalyptus and anisic undertones with minty, sage, parsley, seashore, pepper, rhubarb, woody, sweet, floral, jasmine, caryophyllene-like, mushroomy, waxy and anisic topnotes. |

EXAMPLE VI

PERFUMED LIQUID DETERGENTS

Concentrated liquid detergents (Lysine salt of n-dodecybenzene sulfonic acid as more specifically described in U.S. Pat. No. 3,948,818 issued on Apr. 6, 1976 incorporated by reference herein) with aroma nuances as set forth in Table II of Example V are prepared containing 0.10%, 0.15%, 0.20%, 0.25%, 0.30% and 0.35% of the substance set forth in Table II of Example V. They are prepared by adding and homogeneously mixing the appropriate quantity of substance set forth in Table II of Example V in the liquid detergent. The detergents all possess excellent aromas as set forth in Table II of Example V, the intensity increasing with greater concentrations of substances as set forth in Table II of Example V.

EXAMPLE VII

PREPARATION OF COLOGNE AND HANDKERCHIEF PERFUMES

Compositions as set forth in Table II of Example V are incorporated into colognes at concentrations of 2.0%, 2.5%, 3.0%, 3.5%, 4.0% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example V are imparted to the colognes and to the handkerchief perfumes at all levels indicated.

EXAMPLE VIII

PREPARATION OF SOAP COMPOSITION

100 Grams of soap chips [per sample] (IVORY® produced by the Procter & Gamble Company of Cincinnati, Ohio) are each mixed with 1 gram samples of substances as set forth in Table II of Example V until homogeneous compositions are obtained. In each of the cases, the homogeneous compositions are heated under 8 atmospheres pressure at 180° C. for a period of 3 hours and the resulting liquids are placed into soap molds. The resulting soap cakes, on cooling, manifest aromas as set forth in Table II of Example V.

EXAMPLE IX

PREPARATION OF SOLID DETERGENT COMPOSITIONS

Detergents are prepared using the following ingredients according to Example I of Canadian Patent No. 1,007,948 (incorporated by reference herein):

| Ingredients | Percent by Weight |
|---|---|
| NEODOL ® 45-11 (a $C_{12}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example V. Each of the detergent samples has an excellent aroma as indicated in Table II of Example V.

EXAMPLE X

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and their perfuming material are as follows:

1. a water "dissolvable" paper ("Dissolvo Paper");
2. Adogen 448 (m.p. about 140° F.) as the substrate coating; and 3. an outer coating having the following formulation (m.p. about 150° F.):
   57% C$_{20-22}$ HAPS;
   22% isopropyl alcohol;
   20% antistatic agent; and
   1% of one of the substances as set forth in Table II of Example V, supra.

Fabric softening compositions prepared according to Example I at column 15 of U.S. Pat. No. 3,632,396 having the aroma characteristics as set forth in Table II of Example V, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example V is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added softener non-woven fabrics and these aroma characteristics are described in Table II of Example V, supra.

EXAMPLE XI

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% of food grade ethanol. 8.0 Grams of the polymer is dissolved in the alcohol. The following ingredients are added to the PVP/VA alcoholic solution:

| Ingredients | Percent by Weight |
| --- | --- |
| Dioctyl sebacate | 0.05 |
| Benzyl alcohol | 0.10 |
| Dow Corning 473 fluid (prepared by the Dow Corning Corporation) | 0.10 |
| TWEEN ® 20 surfactant (prepared by ICI America Corporation) | 0.03 |
| One of the perfumery substances as set forth in Table II of Example IV, supra | 0.10 |

The perfuming substances as set forth in Table II of Example V add aroma characteristics as set forth in Table II of Example V which are rather intense and aesthetically pleasing to the users of the soft-feel, good-hold pump hair sprays.

EXAMPLE XII

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of the Union Carbide Corporation) (1.4 weight percent). The resulting melt is admixed with Stepanol WAT produced by the Stephan Chemical Company (35.0 weight percent). The resulting mixture is heated to 60° C. and mixed until a clear solution is obtained (at 60° C.). This material is "COMPOSITION A".

GAFQUAT® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by the Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substance as set forth in Table II of Example V is added to the mixture. The resulting mixture is cooled to 40° C. and blending is carried out for an additional one hour in each case. At the end of this blending period, the resulting material has a pleasant fragrance as indicated in Table II of Example V.

In the following examples, ARCOMOX® DMC-W and AROMOX® DMMC-W are 30% aqueous solutions of dimethyl cocoamine oxide; and ARCMOX® NCMD-W is 40% solution of N-cocomorpholine oxide produced by Armac Division of AKZO of Chicago, Ill. DOWFAX® 2A1 (a Registered Trademark of the Dow Chemical Company of Midland, Mich.) is the compound having the structure:

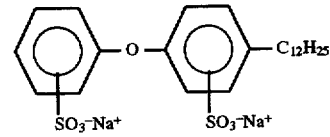

wherein the C$_{12}$H$_{25}$ moiety is branched chain and the SO$_3^-$Na$^+$ moieties are at various positions on each of the benzene rings. DOWFAX® 3B2 is a mixture of compounds defined according to the structure:

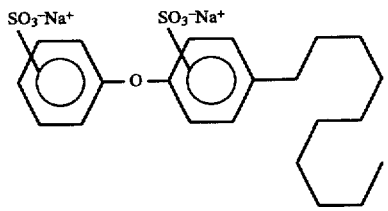

wherein the SO$_3^-$Na$^+$ moieties are at various positions on the phenyl moieties. DOWFAX® 3B2 is a Registered Trademark of the Dow Chemical Company of Midland, Mich.

In the following examples, in place of the DOWFAX® 2A1 and the DOWFAX®3B2, similar materials, for example, the compound having the structure:

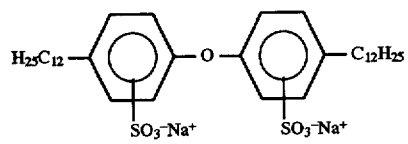

may be used or, generically, the compound defined according to the structure:

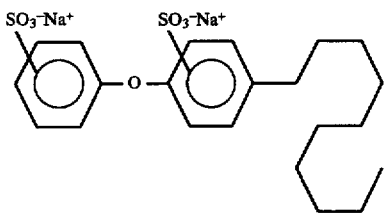

may be used wherein at least one of $R_1$ and $R_2$ is $C_{10}$–$C_{12}$ straight chain or branched chain alkyl and $M_\alpha$ and $M_\beta$ are the same or different and each represents alkali metal selected from the group consisting of lithium, potassium and sodium. Furthermore, AROMOX® DMC-W, AROMOX® DMMC-W and ARCOMOX® NCMD-W are covered by the generic structure:

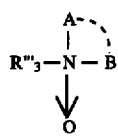

wherein $R_3'''$ is straight chain alkyl; wherein more than 55% of the $R_3'''$ moieties consist of straight chain alkyl having from 11 up to 13 carbon atoms and where A and B are each separately methyl or taken together complete a morpholine ring.

EXAMPLE XIII

Four drops of each of the materials of Table II of Example V is added to 2 grams of AROMOX® DMC-W to produce a clear premix. The clear premix is added to 200 grams of CLOROX® with stirring resulting in a clear, stable, single phase solution. Sufficient 1M (molar) aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor, but does have a faint, pleasant aroma as described in Table II of Example V, supra. Furthermore, no such characteristic "hypochlorite" aroma is retained on the hands of the individual handling such laundry in both the wet and the dry states.

EXAMPLE XIV

AROMOX® DMMC-W in various quantities is mixed with 0.1 gram of each of the compositions set forth in Table II of Example V, supra. The resulting premixes are then added to 200 grams of an aqueous 5% sodium hypochlorite solution. Sufficient 12.5M aqueous NaOH is added to bring the pH of the mixture up to 13. The following results are obtained:

| Percentage AROMOX ® DMMC-W | Clarity of Hypochlorite Solution After Addition of Premix |
| --- | --- |
| 0.25% | Clear after three days |
| 0.18% | Clear after three days |
| 0.05% | Initially, slightly turbid; two phases exist after five days. |

When used as laundry bleaches, the resulting bleached laundries on dry-out in an atmosphere of 50% relative humidity in each of the three cases above retain the aroma as set forth in Table II of Example V, supra; whereas without the use of the materials containing the 7-isopropyl-8,8-dimethyl-6,10-dioxaspiro-$C_{10}$ and $C_{11}$ alkane derivatives of our invention defined according to the structure:

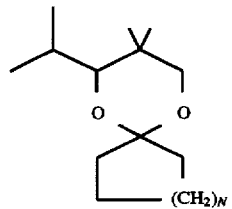

wherein N is 1 or 2, the bleached laundry has a faint characteristic disagreeable hypochlorite aroma.

EXAMPLE XV

Four drops of each of the materials set forth in Table II of Example V is added to 1.5 grams of AROMOX® NCMD-W to produce a clear premix. The clear premix is added to 200 grams of CLOROX® with stirring resulting in a clear, stable, single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor, but does have a faint, pleasant aroma as described in Table II of Example V. Furthermore, no such characteristic "hypochlorite" aroma is retained on the hands of the individual handling such laundry in both the wet and the dry states.

EXAMPLE XVI

One gram of n-tridecyl dimethyl amine oxide is admixed with 8 drops of each of the materials of Table II of Example V, supra. This premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains an aroma as described in Table II of Example V, supra; whereas without the use of the materials containing the compound defined according to the structure:

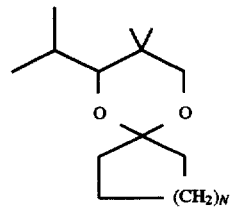

wherein N is 1 or 2, the bleached laundry has a faint characteristic disagreeable "hypochlorite" aroma.

EXAMPLE XVII

DOWFAX® 2A1 in various quantities as set forth below is mixed with 0.1 gram of each of the materials of Table II of Example V, supra. The resulting premixes are then added to 200 grams of an aqueous 7% sodium hypochlorite solution. Sufficient 12.5M aqueous NaOH is added to bring the pH of the mixture up to 13.5. The following results are obtained:

| Percentage DOWFAX ® 2A1 | Clarity of Hypochlorite Solution After Addition of Premix |
|---|---|
| 0.30% | Clear after seven days |
| 0.20% | Clear after five days |
| 0.08% | Clear after three days |
| 0.02% | Initially, slightly turbid; two phases exist after five days. |

EXAMPLE XVIII

One gram of DOWFAX® 3B2, 1 gram of DOWFAX® 2A1 and 0.25 grams of AROMOX® DMMC-W is admixed with 8 drops of each of the materials of Table II of Example V, supra. These premixes are then added with stirring to 200 grams of a mixture containing 4.5% aqueous sodium hypochlorite and 4.5% aqueous lithium hypochlorite. Sufficient 4M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundries on dry-out in an atmosphere of 50% relative humidity retain aromas as set forth in Table II of Example V, supra; whereas without the use of materials containing the compound defined according to the structure:

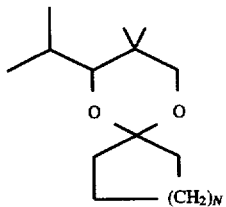

wherein N is 1 or 2 produced according to our invention, the bleached laundry has a faint characteristic disagreeable "hypochlorite" aroma.

EXAMPLE XIX 0.2 Grams of n-tridecyl dimethyl amine oxide and 0.7 grams of DOWFAX® 3B2 are admixed with 8 drops of each of the materials set forth in Table II of Example V, supra. These premixes are then added with stirring to 200 grams of a 7% aqueous solution of lithium hypochlorite. Sufficient 3M aqueous LiOH is added to each material to bring the pH of each of the solutions to 13.4. The mixtures are then heated to 120° F. and maintained at that temperature with stirring for a period of one week. The resulting solutions remain clear in a single phase. When used as a laundry bleach, the resulting bleached laundries on dry-out in an atmosphere of 50% relative humidity retain aromas as set forth in Table II of Example V, supra; whereas without the use of the materials containing the 7-isopropyl-8,8-dimethyl-6,10-dioxaspiro-$C_{10}$ and $C_{11}$ alkane derivatives defined according to the structure:

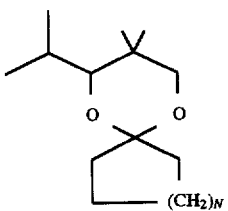

wherein N is 1 or 2, the bleached laundries have faint characteristic disagreeable "hypochlorite" aromas.

EXAMPLE XX

PEROXIDE BLEACH COMPOSITION

A bleaching detergent is formulated containing:

(A) 5 weight percent of an oxygen based bleaching agent generating hydrogen peroxide and water;

(B) 0.2% of a bleach activator having the formula:

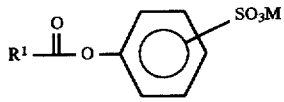

wherein $R^1$ is decyl and wherein M is sodium; and (C) the compound having the structure:

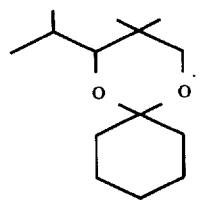

During storage, the resulting composition does not pick up any "off" odor, but has a pleasant aroma as described in Table I, supra.

What is claimed is:

1. A process for imparting, augmenting or enhancing the aroma of a substance selected from the group consisting of perfume compositions, perfumed polymers, soaps, anionic, nonionic, cationic or zwitterionic detergents, fabric softener articles, fabric softener compositions and bleach compositions consisting essentially of the step of adding to said substance an aroma imparting, augmenting or enhancing quantity and concentration of at least one of 7-isopropyl-8,8-dimethyl-6,10-dioxaspiro-$C_{10}$ and $C_{11}$ alkane derivative defined according to the structure:

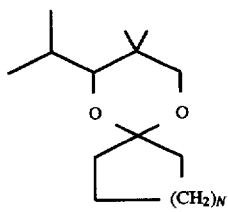

wherein N is 1 or 2.

2. The process of claim 1 wherein N is 1.
3. The process of claim 1 wherein N is 2.
4. The process of claim 1 wherein the substance is a perfume composition.

5. The process of claim 2 wherein the substance is a perfume composition.

6. The process of claim 3 wherein the substance is a perfume composition.

7. The process of claim 1 wherein the substance is an anionic, nonionic, cationic or zwitterionic detergent.

8. The process of claim 1 wherein the substance is a soap.

9. The process of claim 1 wherein the substance is a fabric softener article.

10. The process of claim 1 wherein the substance is a fabric softener composition.

11. The process of claim 1 wherein the substance is a bleach composition.

12. The process of claim 1 wherein the substance is a perfumed polymer.

13. A perfume composition consisting essentially of a non-salicylate-containing perfume base and intimately admixed therewith an aroma augmenting or enhancing quantity and concentration of at least one 7-isopropyl-8,8-dimethyl-6,10-dioxaspiro-$C_{10}$ and $C_{11}$ alkane derivative defined according to the structure:

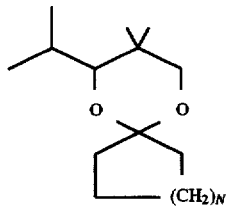

wherein N is 1 or 2.

14. The perfume composition of claim 13 wherein N is 1.

15. The perfume composition of claim 13 wherein N is 2.

16. An aqueous alkali metal hypochlorite solution comprising as a sole detergent a composition of matter selected from the group consisting of (a) at one substance defined according to the structure:

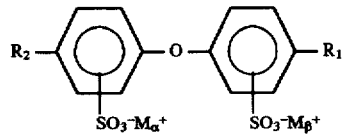

wherein at least one of $R_1$ and $R_2$ is $C_{10}$–$C_{12}$ straight chain or branched chain alkyl; when one of $R_1$ or $R_2$ is $C_{10}$–$C_{12}$ straight chain or branched chain alkyl, the other of $R_1$ or $R_2$ is hydrogen; wherein $M_\alpha$ and $M_\beta$ are the same or different and each represents alkali metal selected from the group consisting of sodium, potassium and lithium; and (2) a mixture comprising a material having the structure:

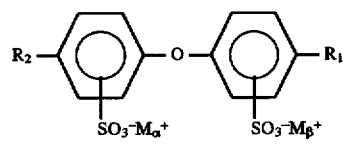

and intimately admixed therewith a substance having the structure:

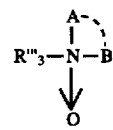

wherein $R_3'''$ is straight chain alkyl; wherein more than 55% of the $R_3'''$ moieties consist of straight chain alkyl having from 11 up to 13 carbon atoms and wherein A and B are each separately methyl or, taken together, complete a morpholine ring; and from 0.02% up to 0.2% of one or more 7-isopropyl-8,8-dimethyl-6,10-dioxaspiro-$C_{10}$ and $C_{11}$ alkane derivatives defined according to the structure:

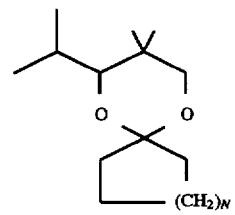

wherein N is 1 or 2, said 7-isopropyl-8,8-dimethyl-6,10-dioxaspiro-$C_{10}$ and $C_{11}$ alkane derivative being capable of imparting to said alkali metal hypochlorite solution or to an article to which the said alkali metal hypochlorite solution is applied a minty and herbal aroma, said alkali metal hypochlorite solution having a pH of 11 up to 14.

17. The composition of claim 16 wherein the compound having the structure:

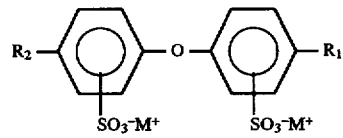

is selected from the group of materials having the structures:

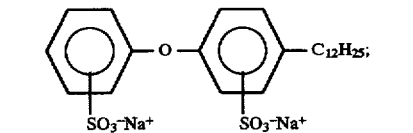

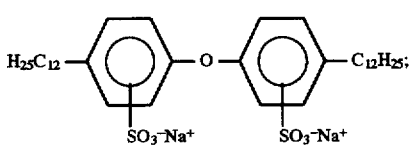

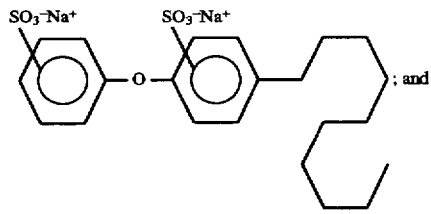

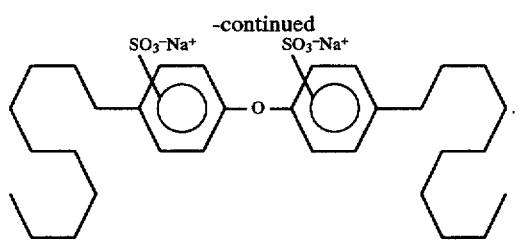

18. A process for producing a stable, single phase aqueous alkali metal hypochlorite solution having a minty and herbal fragrance consisting in sequential orders of the steps of (a) adjusting the pH of an aqueous alkali metal hypochlorite solution to the range of 11–14.0; (b) admixing a composition of matter selected from the group consisting of:

(i) a chemical compound having the structure:

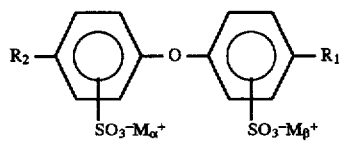

wherein at least one of $R_1$ and $R_2$ is $C_{10}$–$C_{12}$ straight chain or branched chain alkyl and $M_\alpha$ and $M_\beta$ are the same or different and each represents alkali metal selected from the group consisting of lithium, potassium and sodium;

(ii) a mixture of at least one compound having the structure:

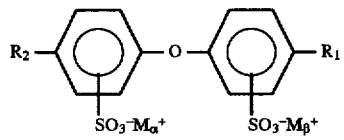

and a compound having the structure:

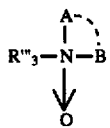

wherein $R_3'''$ is straight chain alkyl; wherein more than 55% of the $R_3'''$ moieties consist of straight chain alkyl having from 11 up to 13 carbon atoms and wherein A and B are each separately methyl or, taken together, complete a morpholine ring with a composition consisting essentially of a 7-isopropyl-8,8-dimethyl-6,10-dioxaspiro-$C_{10}$ and $C_{11}$ alkane derivative having the structure:

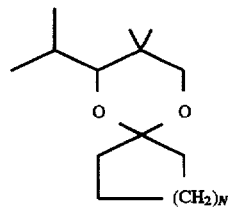

wherein N is 1 or 2; and (iii) adding said premix to the pH-adjusted hypochlorite solution.

19. The process of claim 18 comprising the additional step of adding to said premix a gel-forming agent selected from the group consisting of sodium palmitate, lithium palmitate, potassium palmitate, sodium laurate, lithium laurate, potassium laurate, sodium stearate, potassium stearate and lithium stearate.

20. The composition of claim 16 comprising, in addition to the ingredients of said compostion, a thickening or gel-forming agent selected from the group consisting of sodium laurate, potassium laurate, lithium laurate, sodium palmitate, potassium palmitate, lithium palmitate, sodium stearate, potassium stearate and lithium stearate.

21. A process for producing a 7-isopropyl-8,8-dimethyl-6,10-dioxaspiro-$C_{10}$ and $C_{11}$ alkane derivative having the structure:

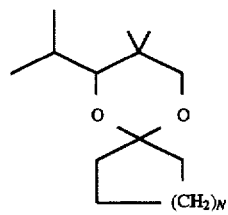

wherein N is 1 or 2 consisting essentially of the sequential steps of:

(i) reacting a cycloalkanone having the structure:

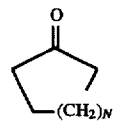

wherein N is 1 or 2 with a tri-lower alkyl orthoformate having the structure:

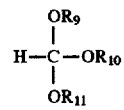

wherein $R_9$, $R_{10}$ and $R_{11}$ are the same or different and each represents methyl or ethyl according to the reaction:

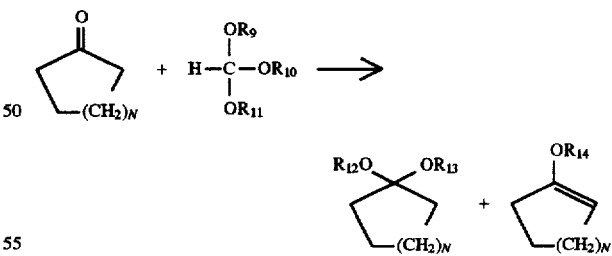

thereby forming the ketal defined according to the structure:

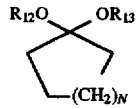

wherein $R_{12}$ and $R_{13}$ are the same or different and each represents methyl or ethyl and wherein the compound having the structure:

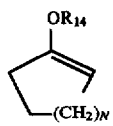

is a single compound wherein $R_{14}$ is methyl or ethyl or a mixture of compounds wherein in the mixture in one of the compounds $R_{14}$ is methyl and in the other of the compounds $R_{14}$ is ethyl, with the proviso that when $R_9$, $R_{10}$ and $R_{11}$ are the same methyl or ethyl then $R_{12}$ and $R_{13}$ are the same methyl or ethyl and $R_{14}$ is the same methyl or ethyl;

(ii) isolating the resulting ketal from the reaction mass defined according to the structure:

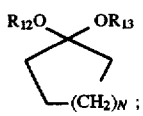

(iii) reacting the thus-formed, isolated ketal with a diol having the structure:

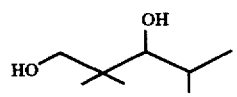

according to the reaction:

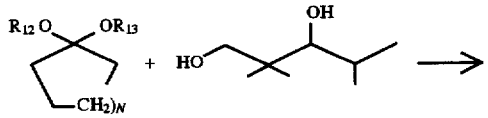

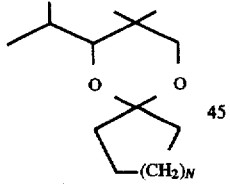

thereby forming the 7-isopropyl-8,8-dimethyl-6,10-dioxaspiro-$C_{10}$ and $C_{11}$ alkane derivative defined according to the structure:

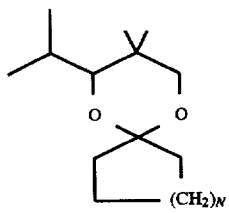

wherein N is 1 or 2; and then (iv) isolating the resulting 7-isopropyl-8,8-dimethyl-6,10-dioxaspiro-$C_{10}$ and $C_{11}$ alkane derivative having the structure:

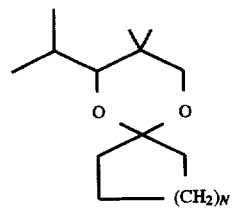

from the reaction mass.

22. The process of claim 21 wherein N is 1.
23. The process of claim 21 wherein N is 2.
24. The process of claim 21 wherein $R_9$, $R_{10}$, $R_{11}$, $R_{12}$, $R_{13}$ and $R_{14}$ each represents methyl.
25. The process of claim 24 wherein N is 1.
26. The process of claim 24 wherein N is 2.
27. A perfume bleach composition containing a bleaching substance selected from the group consisting of:
   (i) an oxygen-based, bleaching agent generating hydrogen peroxide in water;
   (ii) a percarbonate bleaching substance;
   (iii) a perborate bleaching substance; and
   (iv) a manganese-containing bleaching substance
and intimately admixed therewith an aroma imparting quantity and concentration of at least one 7-isopropyl-8,8-dimethyl-6,10-dioxaspiro-$C_{10}$ and $C_{11}$ alkane derivative having the structure:

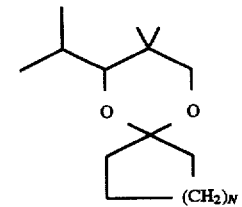

wherein N is 1 or 2.

* * * * *